US008894604B2

(12) United States Patent
Vecellio-None et al.

(10) Patent No.: US 8,894,604 B2
(45) Date of Patent: Nov. 25, 2014

(54) DEVICE FOR ORAL ADMINISTRATION OF AN AEROSOL FOR THE RHINOPHARYNX, THE NASAL CAVITIES OR THE PARANASAL SINUSES

(75) Inventors: Laurent Vecellio-None, Chambray les Tours (FR); Gilles Chantrel, Saint Etienne (FR); Michel Massardier, Saint Etienne (FR)

(73) Assignees: La Diffusion Technique Francaise, Sainte Etienne (FR); Universite Francois Rabelais, Tours (FR)

( * ) Notice: Subject to any disclaimer, the term of this patent is extended or adjusted under 35 U.S.C. 154(b) by 54 days.

(21) Appl. No.: 13/519,620

(22) PCT Filed: Dec. 23, 2010

(86) PCT No.: PCT/FR2010/052896

§ 371 (c)(1), (2), (4) Date: Sep. 27, 2012

(87) PCT Pub. No.: WO2011/080473

PCT Pub. Date: Jul. 7, 2011

(65) Prior Publication Data

US 2013/0008437 A1 Jan. 10, 2013

(30) Foreign Application Priority Data

Dec. 28, 2009 (FR) ..................................... 09 59622

(51) Int. Cl.
*A61M 37/00* (2006.01)
*A61M 15/08* (2006.01)

(Continued)

(52) U.S. Cl.
CPC ............... *A61M 15/08* (2013.01); *A61M 11/02* (2013.01); *A61M 15/0091* (2013.01); *A61M 11/001* (2014.02); *A61M 15/0098* (2014.02); *A61M 11/08* (2013.01); *A61M 2016/0027* (2013.01); *A61M 2205/073* (2013.01); *A61M 2210/0618* (2013.01); *A61M 2210/0625* (2013.01); *A61M 2210/0681* (2013.01)
USPC ............................................. 604/26; 604/27

(58) Field of Classification Search
CPC .......... A61M 11/005; A61M 15/0091; A61M 15/08; A61M 2011/007; A61M 2015/0098; A61M 2016/0021; A61M 2202/064; A61M 2205/071; A61M 2205/073; A61M 2205/13
USPC ....................... 604/26, 27, 503, 505, 514, 58
See application file for complete search history.

(56) References Cited

U.S. PATENT DOCUMENTS 6,752,147 B1 6/2004 Goldemann et al.
2005/0235992 A1 10/2005 Djupesland (Continued)

FOREIGN PATENT DOCUMENTS

EP 1410820 A2 4/2004
FR 2638361 A1 5/1990

(Continued)

OTHER PUBLICATIONS

International Search Report for PCT/FR2010/052896 dated Apr. 26, 2011.

(Continued)

*Primary Examiner* — Kevin C Sirmons
*Assistant Examiner* — Deanna K Hall
(74) *Attorney, Agent, or Firm* — Heslin Rothenberg Farley & Mesiti P.C.

(57) ABSTRACT

A device for administration of an aerosol includes a generator of particles of size between 10 nm and 200 um, a mouthpiece or mouth mask for oral administration of the aerosol during the nasal exhalation phase or during the respiratory pause phase preceding nasal exhalation, and a source of gas or pressure for conveying the particles. The mouthpiece is airtight, extends beyond the teeth of the patient by a maximum length of 4 cm, and administers the aerosol for the nasal cavities, the rhinopharynx or the paranasal sinuses during aerosol administration phases, such that the is successively applied to the mouth, the rhinopharynx and then the nasal fossae and the sinuses, and then the aerosol escapes via one or both of the patient's nostrils. The device does not allow exhalation via the mouth during aerosol administration phases, and the aerosol particles not being directed to the lungs.

12 Claims, 18 Drawing Sheets

(51) Int. Cl.
*A61M 11/02* (2006.01)
*A61M 15/00* (2006.01)
*A61M 11/00* (2006.01)
*A61M 11/08* (2006.01)
*A61M 16/00* (2006.01)

(56) References Cited

U.S. PATENT DOCUMENTS

| | | |
|---|---|---|
| 2006/0096589 A1 | 5/2006 | Djupesland |
| 2006/0107957 A1 | 5/2006 | Djupesland |
| 2006/0162722 A1 | 7/2006 | Boehm et al. |
| 2007/0181133 A1 | 8/2007 | Boehm et al. |
| 2008/0223363 A1* | 9/2008 | Djupesland ............. 128/200.23 |

FOREIGN PATENT DOCUMENTS

| | | |
|---|---|---|
| FR | 19930013478 | 5/1995 |
| FR | 2835435 A1 | 8/2003 |
| WO | 98/53869 A1 | 12/1998 |
| WO | 02/13896 A1 | 2/2002 |
| WO | 02/068031 A2 | 9/2002 |
| WO | 03000310 A2 | 1/2003 |
| WO | 2004/103447 A2 | 12/2004 |
| WO | 2005/120617 A1 | 12/2005 |
| WO | 2007093784 A1 | 8/2007 |

OTHER PUBLICATIONS

Cheng, et al; "Characterization of Nasal Spray Pumps and Deposition Pattern in a Replica of the Human Nasal Airway," Journal of Aerosol Medicine, vol. 14, No. 2, 2001, pp. 267-280.
Croce, et al; "In Vitro Experiments and Numerical Simulations of Airflow in Realistic Nasal Airway Geometry," Annals of Biomedical Engineering, vol. 34, No. 6, Jun. 2006, pp. 997-1007.
Djupesland, et al; "Bi-Directional Nasal Delivery of Aerosols Can Prevent Lung Deposition," Journal of Aerosol Medicine, vol. 17, No. 3, 2004, pp. 249-259.
Guo, et al; "The Effect of Formulation Variables and Breathing Patterns on the Site of Nasal Deposition in an Anatomically Correct Model," Pharmaceutical Research, vol. 22, No. 11.
Kimbell, et al; "Characterization of Deposition from Nasal Spray Devices Using a Computational Fluid Dynamics Model of the Human Nasal Passages," Journal of Aerosol Medicine, vol. 20, No. 1, 2007, pp. 59-74.
Laurent Vecellio-None, Doctoral Thesis, Dec. 20, 2002.
Suman, et al; "Comparison of Nasal Deposition and Clearance of Aerosol Generated by a Nebulizer and an Aqueous Spray Pump," Pharmaceutical Research, vol. 16, No. 10, 1999, pp. 1648-1652.

\* cited by examiner

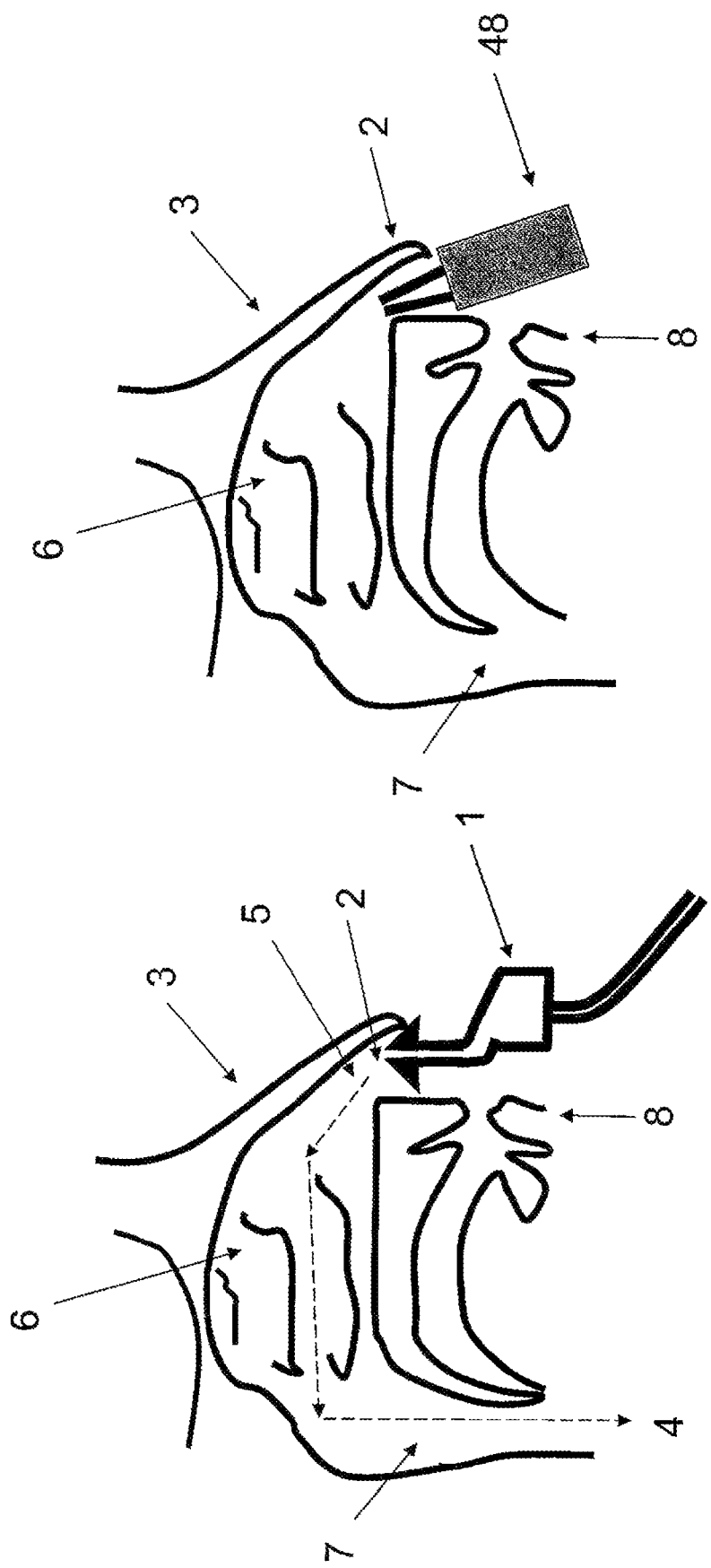

particules
- - ▶ gaz

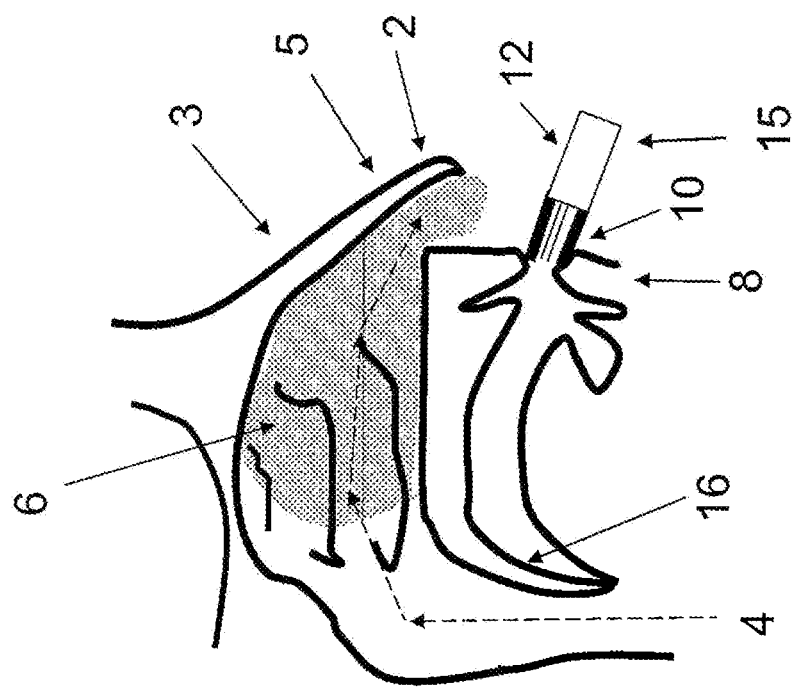
Figure 10
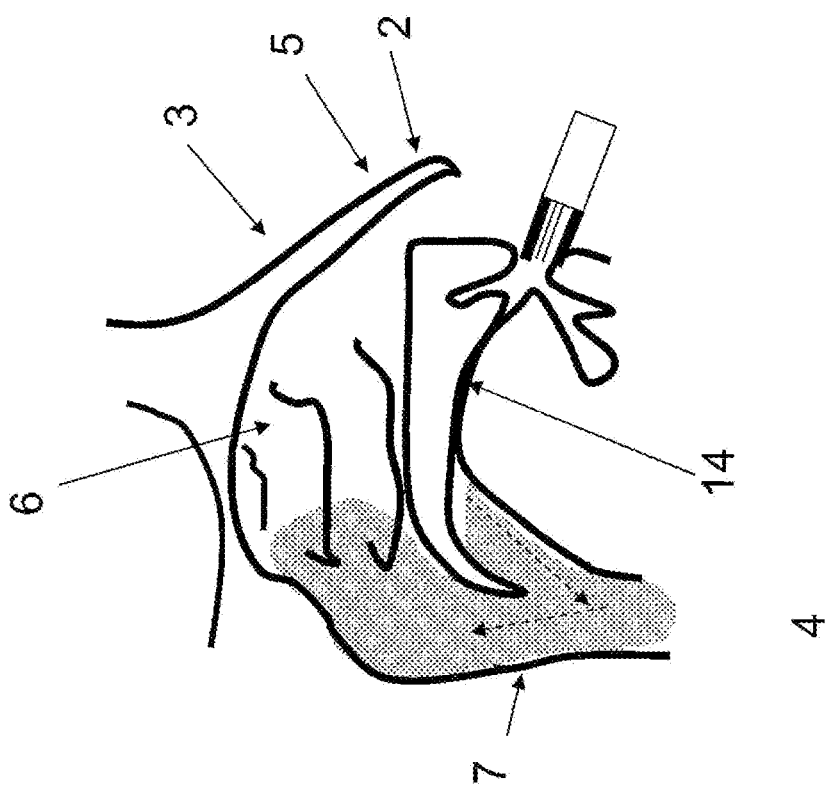
Figure 9
particules
gaz

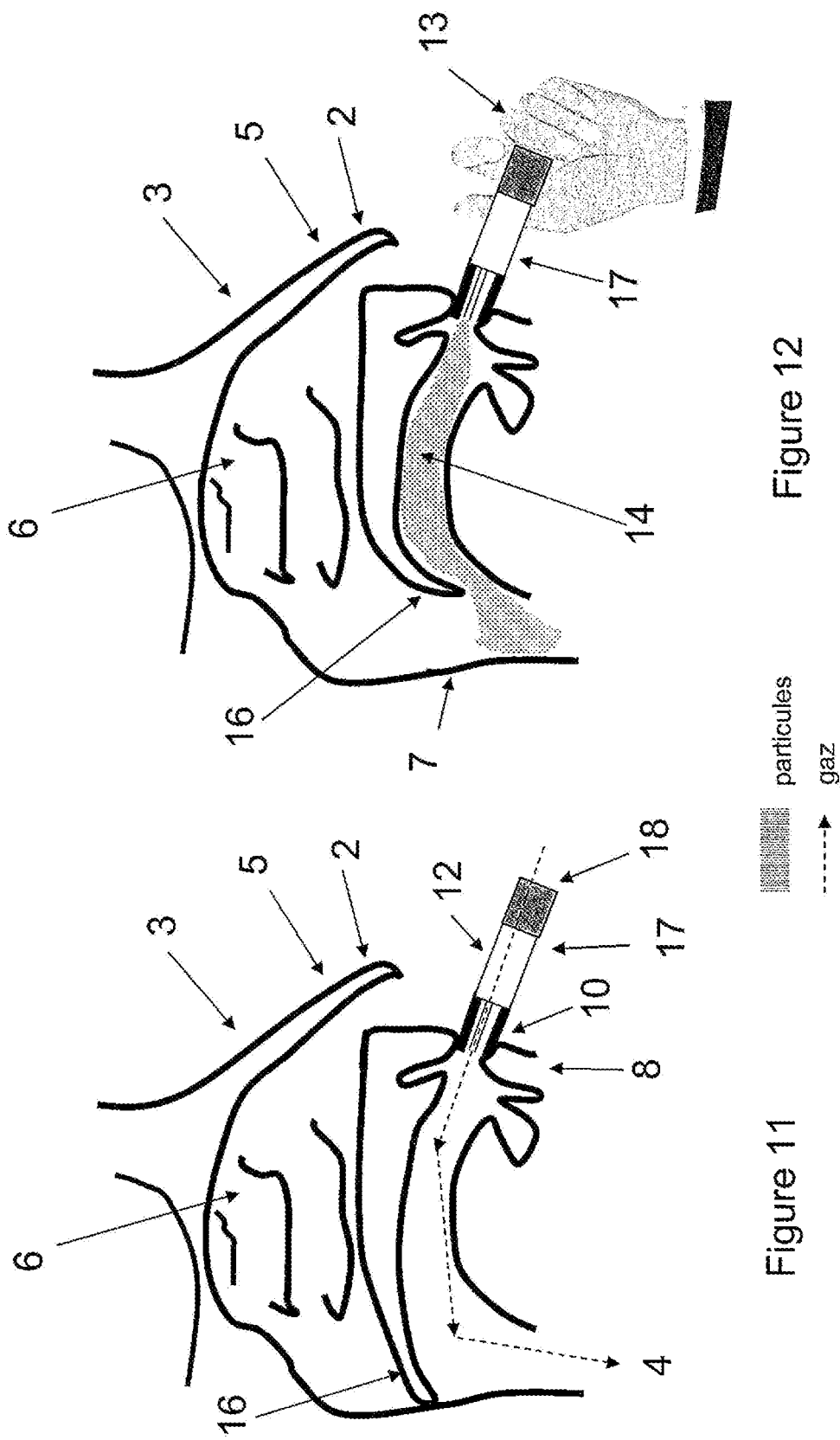

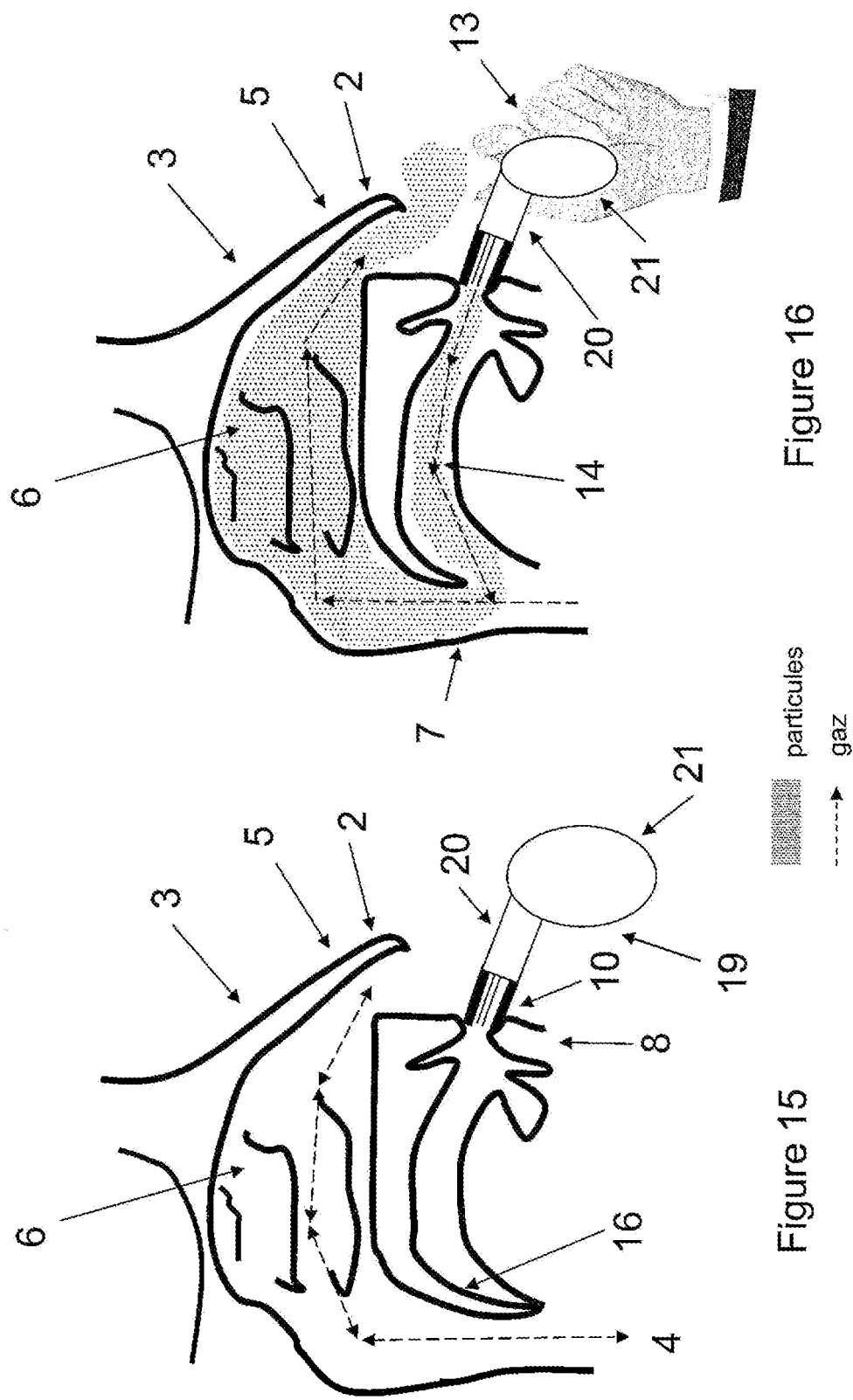

particules
→ gaz particules
gaz

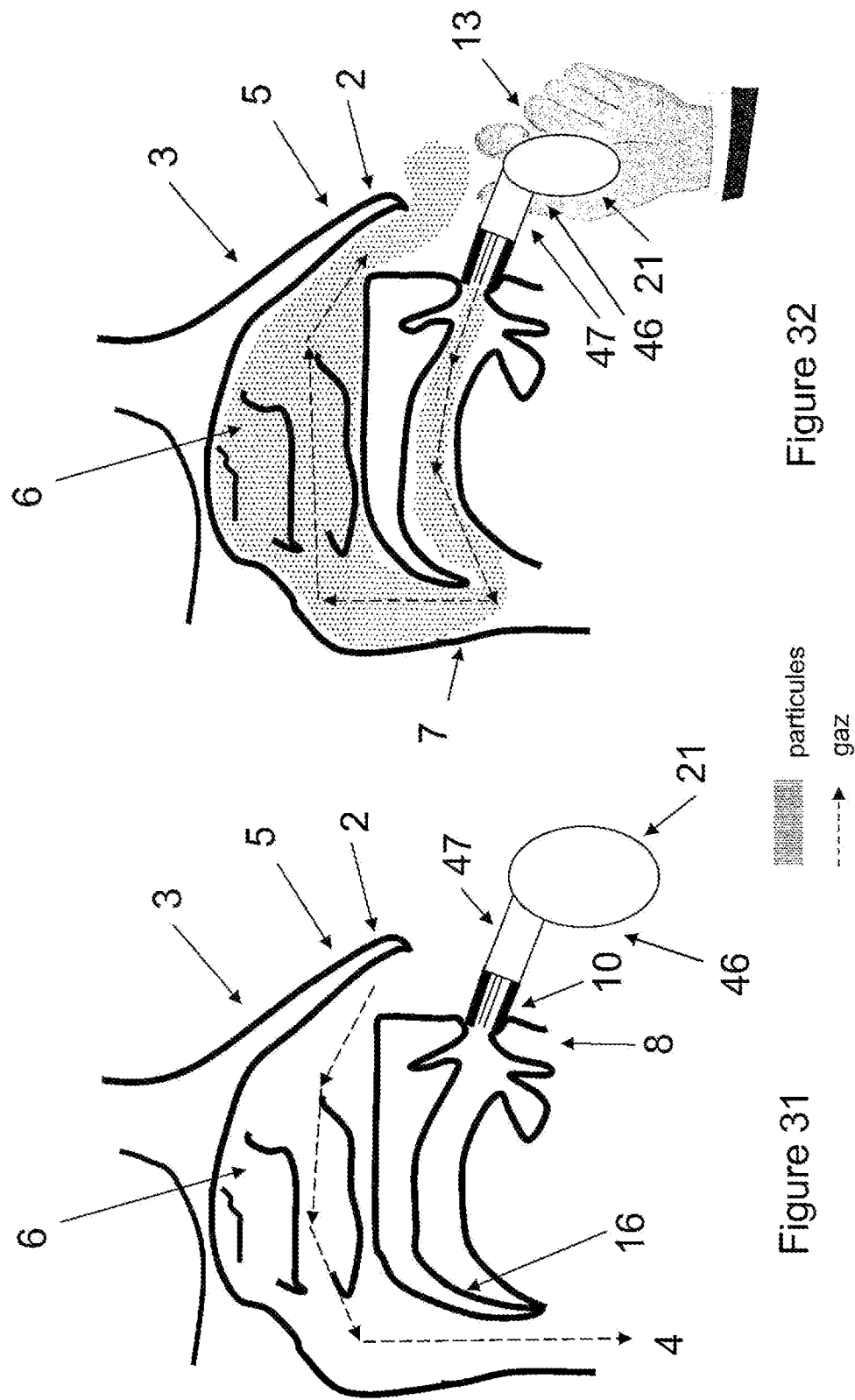

particules
- - -> gaz

DEVICE FOR ORAL ADMINISTRATION OF AN AEROSOL FOR THE RHINOPHARYNX, THE NASAL CAVITIES OR THE PARANASAL SINUSES

CROSS REFERENCE TO RELATED APPLICATIONS

This application is a national stage filing under section 371 of International Application No. PCT/FR2010/052896 filed on Dec. 23, 2010, and published in French on Jul. 7, 2011 as WO 2011/080473 A1 and claims priority of French application No. 0959622 filed on Dec. 28, 2009, the entire disclosure of these applications being hereby incorporated herein by reference.

BACKGROUND ART

This invention relates to the technical sector of systems for the generation of aerosols and sprays for medical purposes.

Aerosols are defined as a suspension of particles in a gas. These particles can range in size from a few nanometers to several tens of micrometers. The purpose of systems for the generation of medical aerosols is to transform medications, a liquid or a powder, into aerosol form to be administered into the respiratory tracts.

The advantage of the aerosol method compared to other methods of administration is the targeting of the organ to be treated by deposition of the medication. Existing nebulizers enable large quantities of medication to be administered into the respiratory tracts. Pulmonary nebulizers target the lungs, nasal nebulizers or sprays target the nasal fossae and the rhinopharynx. As regards nasal nebulizers or sprays, it is theoretically possible to deposit aerosol solely in the nasal fossae, site of the first passage of the aerosol into the airways. A first solution is to use an aerosol with large-sized particles. The problem with an aerosol with a large particle size is that it will not deposit itself in a peripheral and homogenous way in the different compartments of the ENT environment (e.g.: sinus, target site for treating sinusitis) (Suman et al, Pharm Res. 1999, 6:1648-52). The other solution consists in using an aerosol with small-sized particles to try and ensure a "peripheral" deposition in the ENT environment. Moreover, this fine aerosol is capable of depositing itself in the lungs. On the other hand, bearing in mind the anatomy of the nostrils and the rhinopharynx, aerosols penetrating into the nostril will be filtered by the nasal hairs and undergo high acceleration due to the small diameter of the nostrils and the nasal valve (C Croce et al, Ann Biomed Eng. 2006, 34:997-1007). The particles thus conveyed beyond the first centimeters of the nasal fossae will be of a small size incompatible with a deposition by impaction or sedimentation in the rhinopharynx or the sinuses. According to a study conducted with a model head inhaling a 5 µm MMAD aerosol, 82% of the aerosol is deposited in the nose, the nasal valve and the first few centimeters of the nasal fossae, 0.2% in the sinuses, 1% in the rest of the nasal fossae and 26.8% in the lungs (Vecellio, 2002, doctoral thesis). Thus, according to this study by scintigraphic imagery in a plastinated head, only 5% of the aerosol passing through the nasal valve is deposited there.

In the present text, the upper nasal airways can be described as the succession of the following anatomical regions (FIG. 1): the nostrils (2), the nasal valve (5), the nasal fossae (6) and the rhinopharynx (7). The nasal fossae represent the largest anatomical volume and include the ethmoid region, the conchae and the access to the sinus.

The Atomisor NL11 (FR2835435) pneumatic nebulizer poses this problem of targeting the nasal fossae (FIG. 1). In its principle of use, the Atomisor N11 pneumatic nebulizer (1) fitted with its nosepiece (FR2638361) is connected to both nostrils (2), right and left, and generates a 5 µm aerosol in the patient's ENT environment (3) during the inspiratory phase (FIG. 1). During the inspiratory phase (FIG. 1), the aerosol produced by the nebulizer (1) is then directed straight from the ENT environment (3) to the patient's lungs (4). The aerosol produced is then accelerated into the first few centimeters of the nasal fossae and even beyond to the nasal valve (5), which explains its heavy impaction in the first few centimeters of the nostrils. Moreover, the hairs, the first natural element of protection of the respiratory tracts by filtration, intercept the largest particles. The smallest particles having passed through the nasal valve reach the nasal fossae (6), which have a less favourable anatomy for the deposition of particles by impaction than that of the nostrils (slower air speeds than in the nostrils).

Nasal sprays (48) use a nosepiece of sufficient length to ensure the passage of a device through the hairs (FIG. 2). This type of device produces large-sized particles (20 µm to 150 µm) with high speeds of the initial particles ensuring their deposition by impaction. The angle of the spray is therefore an important parameter for ensuring homogeneity of deposition in the rhinopharynx. As described in the literature (Kimbell et al, 2007, J Aerosol Med, 20:59-74), this type of device of administration by spray has limits in its variability of use. In fact, the position and angle of orientation of the device's nosepiece affect the deposition of particles and so the effectiveness of treatment. Moreover, considering the size of the particles and the speed of injection of the particles, it would appear that the particles only just reach the middle nasal fossae (Senocak et al, 2005, Otolaryngology Head and Neck Surgery, 133:944-948) and do not reach the posterior nasal fossae at all (Cheng et al, 2001, J Aerosol Med, 14:267-280) (Guo et al, 2005, Pharm R, 22:1871-1878).

In order to resolve this problem of targeting fine aerosol into the ENT environment, different systems available on the market propose more or less effective solutions.

The PARI Sinus nebulizer implements Patents US2006/0162722 A1 and US2007/0181133 A1. It administers fine aerosol through one nostril, when the patient closes the soft palate, to limit deposition in the lungs and increase deposition in the ENT environment. The aerosol penetrates into one nostril and exits through the other nostril provided with a second nosepiece having a narrow section to increase nasal pressure and promote the penetration of aerosol into the sinuses. This method of administration of the aerosol requires the active participation of the patient. The patient must not inspire or expire during administration of the aerosol and must simultaneously raise his soft palate. As this system demands a very active participation of the patient it can be ineffective if the patient fails correctly to follow the instructions for raising his soft palate. This requires patients to be taught and trained, which is not always achievable due to age constraints. This system does not overcome the heavy deposition in the first few centimeters of the nostrils.

The Optinose system, covered by Patents WO 03/000310 A2, EP1410820A2, US 2006/0107957 A1, US2005/0235992 A1 and US 2006/0096589 A1, also uses the system of penetration of the aerosol into one of the two nostrils and its escape through the other nostril. It also uses an automatic triggering of aerosol generation during the patient's oral expiration phase. Under these conditions, during the inspiration phase, the patient can inspire through the nostril and inhale air containing no aerosol. During the oral expiration phase, the soft palate is raised, and the aerosol produced penetrates into one of the two nostrils. The aerosol is then conveyed from the first nostril to the second nostril and the lungs are protected from any penetration of the aerosol by the seal of the soft palate. The high performance of this system for limiting lung deposition has been proved on healthy patients but the aerosol does not penetrate though a mouthpiece but always through a nosepiece. (Djupesland et al, Bi-directional nasal delivery of aerosols can prevent lung deposition. J Aerosol Med. 2004 Fall; 17(3):249-59). Patent WO2007093784 of the same company also describes a system for aerosol generation only during the nasal expiration phase. The drawback of this system is that the aerosol penetrates through one nostril and not through the mouth, thus the system does not resolve the problem of heavy deposition of aerosol in the first few centimeters of the nostrils.

According to the prior art, it must be acknowledged that the administration of aerosol for the rhinopharynx, nasal cavities or paranasal sinuses is always achieved by means of a nosepiece inserted into the nostrils. This method of administration through the nose is the logical consequence of studies proving the advantage of using a mouthpiece to promote lung deposition. In fact, using a face mask on the patient not only enables inhalation of the aerosol through the mouth but also through the nose, thus limiting lung deposition and promoting rhinopharyngeal deposition. The use of a mouthpiece is therefore recommended for the administration of aerosol for the lungs (Dautzenberg B, Becquemin M H, Chaumuzeau J P, Diot P. 2007. Good practices of aerosol therapy by nebulization. Rev Mal Respir. 24:751-757) and a mouthpiece is recommended for the administration of aerosol for the rhinopharynx. To summarise, the administration of aerosol for the lungs is achieved through the patient's mouth or nose and the administration of aerosol for the nasal cavities is achieved through the patient's nose (Table 1).

TABLE 1

Aerosol generators of the prior art and their means of delivery depending on the respiratory organ to be treated.

| Aerosol penetration organ | Aerosol for the lungs | Aerosol for the rhinopharynx, nasal cavities or paranasal sinuses |
| --- | --- | --- |
| Mouth | Mouthpiece (prior art) | Mouthpiece (Invention) |
| Nose | Face mask (prior art) | Nosepiece (prior art) |

Also known, through Patent WO 2004/103447, is a device provided with a mouthpiece and an administration tube penetrating deep into the oral cavity in order to ensure deposition of the substance by spraying onto the mucosa or the oral cavity, thus with a targeted projection having an effect limited to a given place.

Also known, through Patent WO 98/533869, is a method for introducing a substance into the nose of a person by using a tubular device in the form of a straw inserted at its first opening into the patient's mouth and at its second opening into the patient's nostril. The patient expires through the mouth into the tubular device so as to transfer the substance into the nostril. During the oral expiration phase the soft palate is raised, sealing the communication between the oral cavity and the nasal cavity. The substance can penetrate into the nasal cavity without the risk of deposition in the patient's oral cavity or lungs. This method is physically impossible in the opposite direction.

These documents therefore have very limited applications and effects.

The Applicant's approach has therefore been to reconsider the problem of this targeting of the ENT environment with an aerosol.

Faced with this situation, the Applicant therefore focused on a different design of this type of equipment.

BRIEF SUMMARY OF INVENTION

According to a first characteristic, the aerosol generation system is remarkable in that it consists of an aerosol generator delivering aerosol by means of a mouthpiece to the patient's mouth to treat the rhinopharynx, sinuses, nasal fossae and nostrils (Table 1).

The term mouthpiece used here covers a piece or connection penetrating into the mouth as well as an oral mask applied over the mouth.

According to another characteristic, the aerosol administration device consisting of a generator of particles of which the size is between 10 nm and 200 µm, a mouthpiece or oral mask for oral administration of the aerosol during the nasal expiration phase or during the respiratory pause phase preceding nasal expiration, and a source of gas or pressure for conveying the particles, is remarkable in that the mouthpiece is airtight and penetrates beyond the patient's teeth by a maximum length of 4 cm and constitutes the means of administration of aerosol for the nasal cavities, rhinopharynx or paranasal sinuses during the administration of the aerosol, making it possible for the aerosol to be successively conveyed to the mouth, rhinopharynx then the nasal fossae and sinuses, and then said aerosol to escape through one or both of the patient's nostrils, and in that the device does not allow oral expiration during the aerosol administration phases, the aerosol particles not being directed to the lungs.

BRIEF DESCRIPTION OF DRAWING FIGURES

These and further characteristics will emerge clearly from the following description.

FIG. 1 shows the prior art for nasal delivery with a nebulizer.

FIG. 2 shows the prior art for nasal delivery with a spray.

FIGS. 7, 8, 9 and 10 show the principle of the aerosol administration method according to the invention using a spray type device activated manually and allowing neither expiration nor inspiration through the mouth.

FIGS. 11, 12, 13 and 14 show the principle of the aerosol administration method according to the invention using a valved spray type device activated manually not allowing expiration through the mouth.

FIGS. 15 and 16 show the principle of operation of the system according to the invention using a generator of the powder type with an external gas reservoir for the manual delivery of the aerosol.

FIGS. 31, 32, 33 and 34 show the principle of operation of the system according to the invention with a powder generator and an external gas reservoir for the manual delivery of the aerosol during the first part of the inspiratory pause.

DETAILED DESCRIPTION

Figure 4:
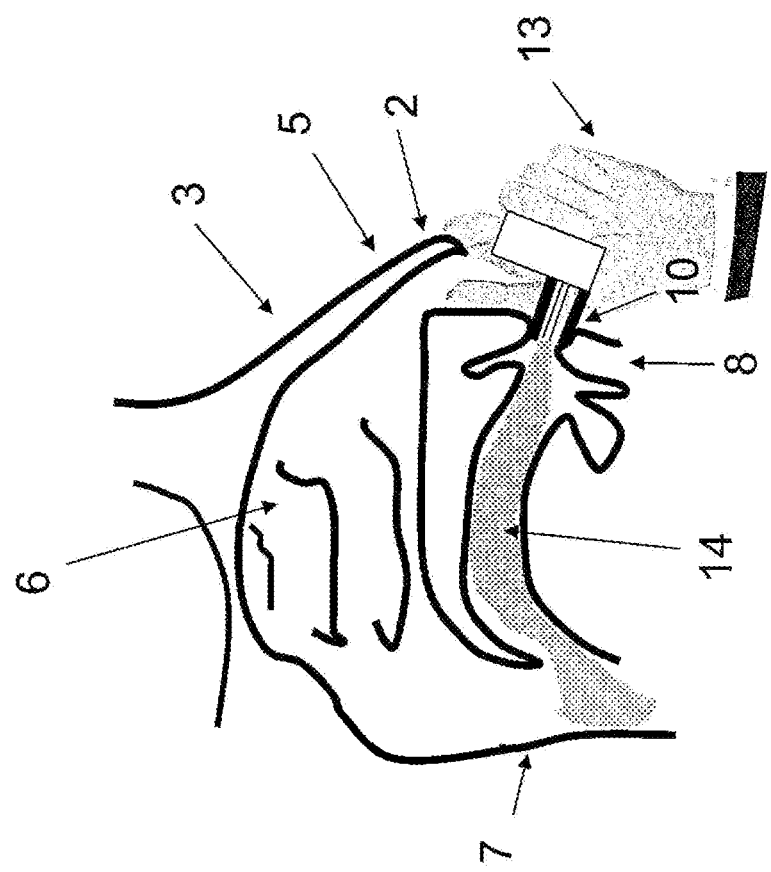
FIGS. 3, 4, 5 and 6 show the principle of the aerosol administration method according to the invention allowing inspiration and expiration through the mouth outside the aerosol administration phases.

The patient's respiration can be broken down into different phases: the inspiratory phase corresponding to the penetration of the outside air into the patient's lungs, the inspiratory pause corresponding to a pause in the patient's respiration at the end of his inspiration, the expiratory phase corresponding to the evacuation of the air contained in his lungs out of the patient and the expiratory pause corresponding to a pause in the patients respiration at the end of his expiration. The invention relates to a method for delivering aerosol into the patient's mouth by means of a mouthpiece for targeting and treating the rhinopharynx, the sinuses, the nasal fossae and the nose. The invention also relates to a system of aerosol administration delivering the aerosol by means of a mouthpiece into the patient's mouth during his nasal expiratory phase or during the respiratory pause phases. This administration can be achieved during all or during the first part of these phases. The invention therefore relates to a method and means for the administration of a nasal aerosol via the second opening of the respiratory organs with the ambient air which is the mouth. The lung (4) is a deformable structure, ensuring the penetration of the air via the mouth (8) or the nose (2) by its modifications of volumes. To reach the lung with the aid of an aerosol, it is necessary to pass through the trachea. There is only one opening in the lung to penetrate therein. In the case of the ENT environment, the situation is different. The ENT environment is a structure that can be regarded as non-deformable and having two openings in contact with the ambient air. It is therefore theoretically possible to make the aerosol penetrate through one opening or through the other opening. The first opening is formed by the nostrils (2) and poses the above-described problems of deposition of aerosol. The second opening is the mouth (8) and is traditionally used for the administration of aerosol for the lungs. The anatomical comparison of these two openings shows the advantage of the passage of aerosol through the mouth (8) (passing through the rhinopharynx (7)) to ensure the penetration of the largest particles into the nasal fossae (6).

Aerosol generation systems are conventionally divided into two main categories, nebulizers and metered-dose inhalers. Nebulizers are devices that generate large quantities of liquid in aerosol form. They require prior preparation by introducing medication into the reservoir of the nebulizer and are used for patients whose pathology is severe. In contrast to nebulizers, metered-dose inhalers are devices that deliver small, calibrated quantities of aerosols. The latter can be powder-based (powder-dose inhaler) or liquid-based (sprays) and offer the advantage of being portable and often prepacked with the medication. These metered-dose inhalers are used for patients whose pathology is stable.

For the description of the present invention, we will distinguish aerosol generators according to whether they use gas or a pressurised liquid to generate the aerosol. Thus, pneumatic nebulizers and pressurised metered-dose inhalers are aerosol generators using pressurised gas. Similarly, certain sprays are also produced with the aid of an overpressure of liquid. By contrast passive powder-dose inhalers, sieve (or membrane) nebulizers and ultrasonic nebulizers are aerosol generators that require neither gas nor pressurised liquid to generate the aerosol.

The particles comprising the aerosol can be moved by means of the vector gas of the aerosol. The particles can also be moved by their initial ejection during their pressurised generation phase. This initial non-zero speed creates a movement of the particle from the generator to the patient's mouth. Thus the conveyance of particles from the generator to the patient's mouth can be achieved by the generator itself (initial speed of the particle) or by the vector gas. The movement of the gas can be achieved by a mechanical means such as for example a ventilator, a compressor or even a manual-action "bulb" (deformable structure). The movement of the particle can be achieved by means of a pressurised liquid (syringe for example). The administration of the aerosol into the patient's mouth during the phases of respiratory pauses or during the nasal expiratory phases can be achieved by the patient himself (for example, manual triggering) or automatically by the system. The automation can be achieved by means of a sensor (of pressure or flow rate for example) or even by the aid of a mechanical means (U.S. Pat. No. 9,313,478 of the present applicant for example). The sensor can be placed on the circuit connected to the mouth or on the circuit connected to the nostrils of the patient. In the case of an aerosol generator operating by means of a source gas, the automation system will trigger the generation of the source gas during the patient's nasal expiratory phases or even during the respiratory pause phases. The aerosol will then be both generated and conveyed by the source gas.

The system will also be capable of generating the aerosol, continuously or not, in a storage chamber, from where it will be conveyed to the patient only during the nasal expiratory phases or during the respiratory pause phases.

In the case of an aerosol generator not requiring the use of source gas for the generation of particles, the system will trigger either the generation of particles, or a movement of gas to convey the particles to the patient's mouth or both.

The oral administration of the aerosol will not be performed during the inspiratory phase of the patient. This can be ensured with the aid of an automatic means administering the aerosol or even by the patient himself triggering the administration of the aerosol during his nasal expiratory phase or during his respiratory pause. In this case, the effectiveness of the treatment will depend on the proper performance of administration of the aerosol by the patient during his respiratory phase. The administration system can also be closed and sealed so as not to permit expiration by the patient through the mouth, but only expiration through the nose.

The invention can be represented in its simplest configuration by a device comprising a generator of particles of which the size is between 10 nm and 200 μm and a mouthpiece.

Figure 3:
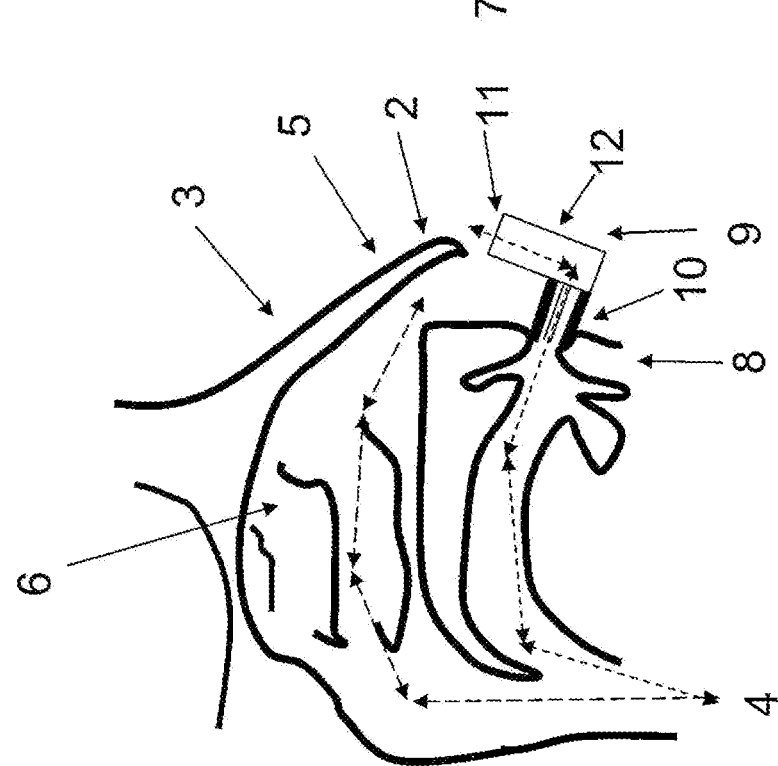

Thus, according to the invention and in a simple embodiment (FIG. 3), the device (9) is an open circuit connected to the patient's mouth (8) comprising a mouthpiece (10) provided with an opening (11) to the ambient air and connected to a generator (12) delivering particles with an initial speed and operating without the addition of gas.

Figure 6:
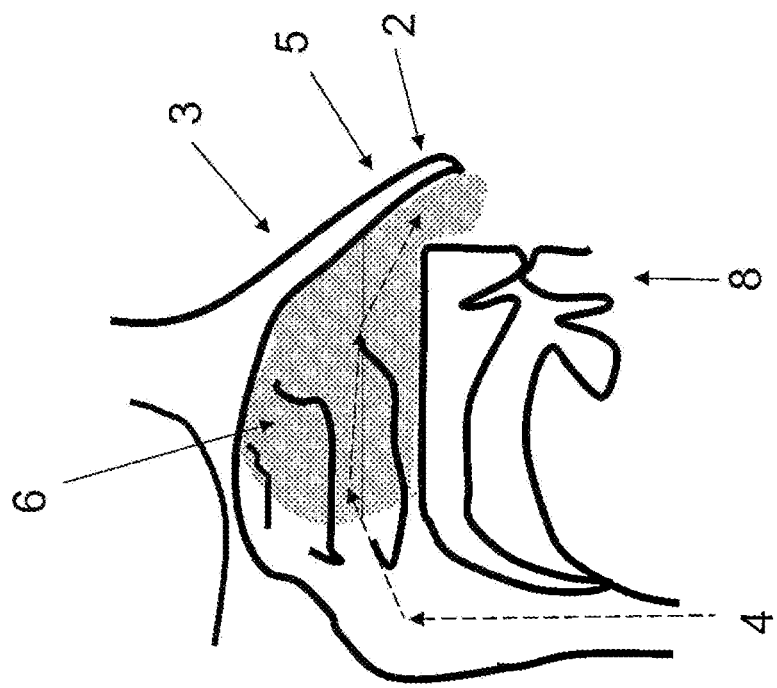
Figure 5:
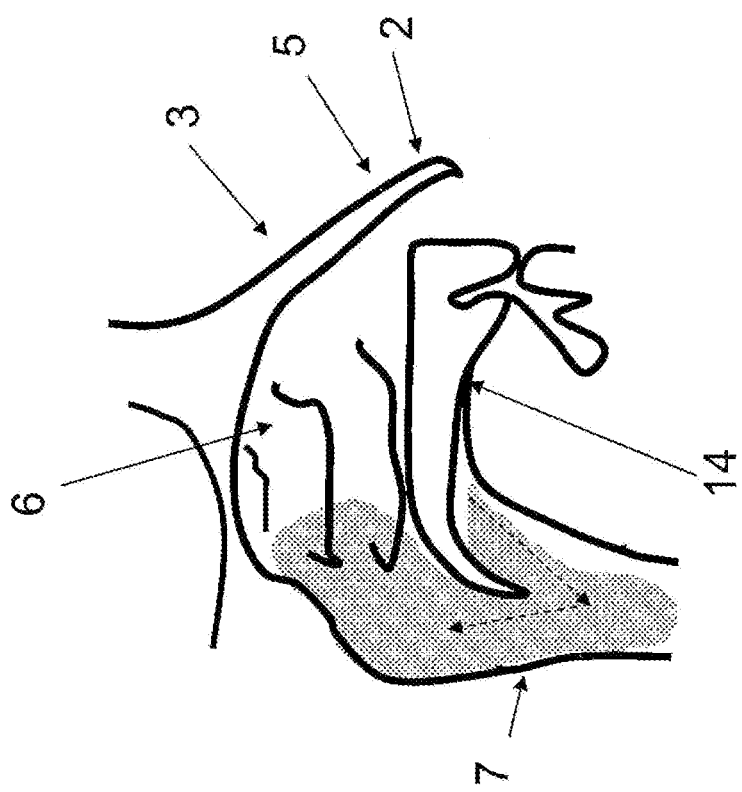
Figure 8:
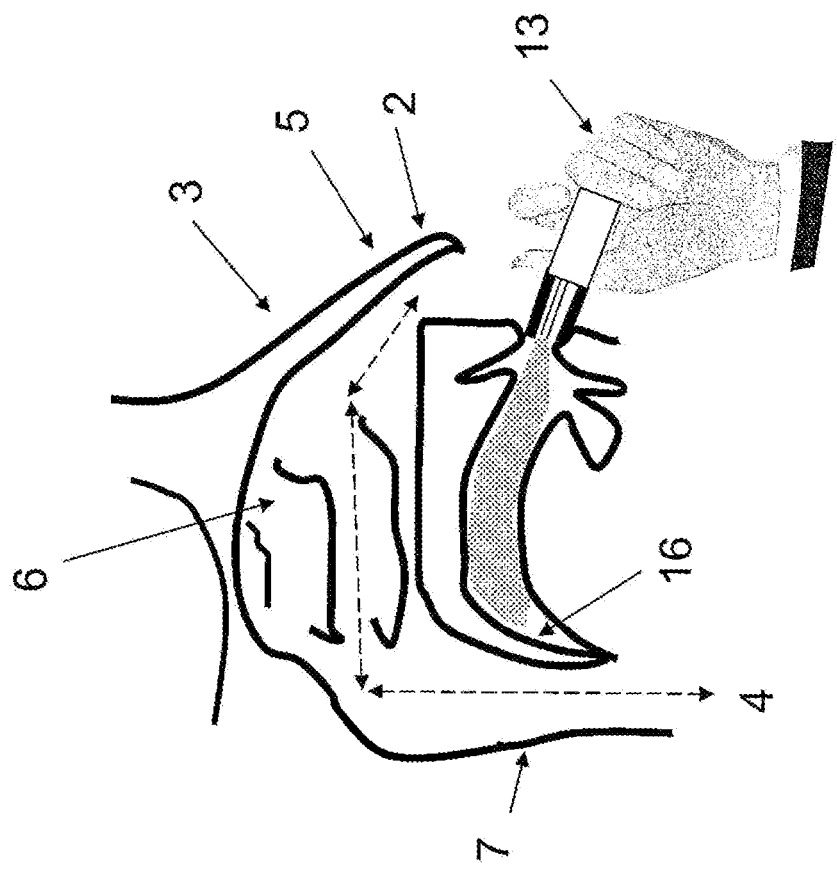
Figure 7:
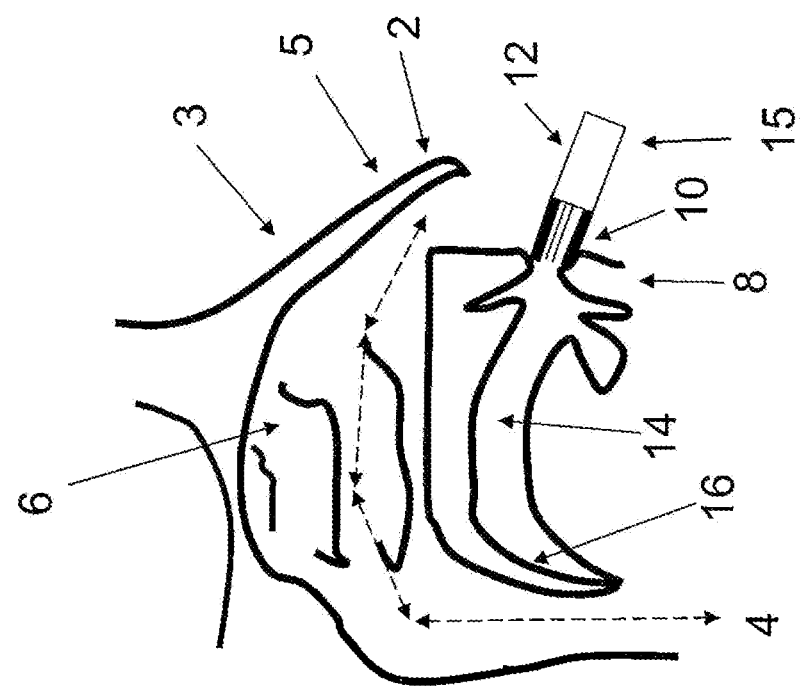
Figure 14:
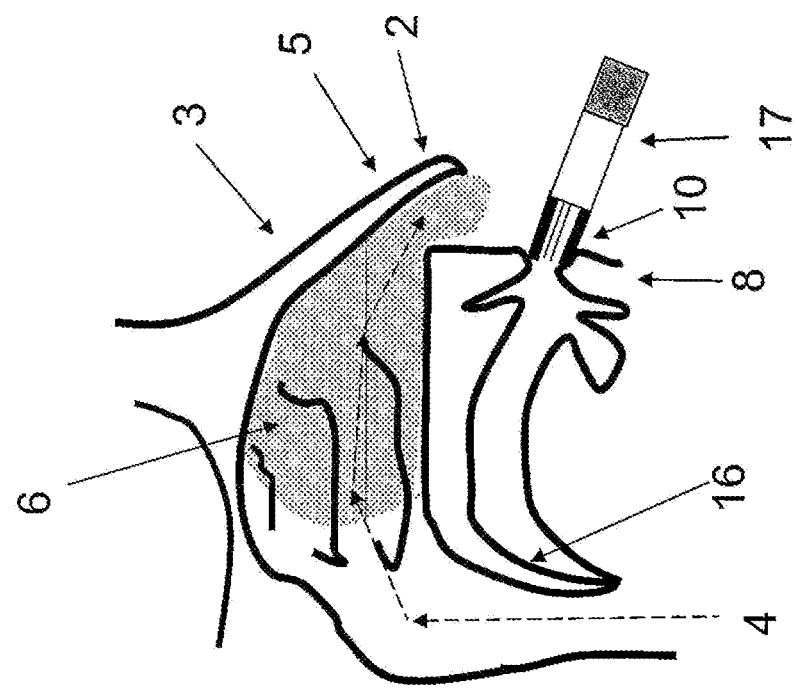

Thus, the system (9) is an open circuit allowing inspiration and expiration through the nose and mouth. During the inspiratory phase (FIG. 3), the patient can inspire freely through the mouth (8) or through the nose (2). The patient must not trigger the administration of the aerosol. The air inspired and penetrating into the patient's lungs (4) contains no aerosol. After the inspiratory phase, the patient performs an apnea (FIG. 4), and must simultaneously trigger the administration of the aerosol (by manual pressure (13) on the device for example). The particles are generated at the patient's mouth (8) and are conveyed by their initial speeds to the oral cavity (14) and the rhinopharynx (7). The patient can then withdraw the device from his mouth then close his lips while remaining in a state of apnea (FIG. 5). He then performs a closing movement of the oral cavity (14) from the front backwards (with the jaw for example) in order to create a change in volume so as to generate an overpressure and move the aerosol towards the rhinopharynx (7). The patient can then (or simultaneously) expire (FIG. 6) freely through the nose to convey the particles from the rhinopharynx (7) to the nostrils (2), passing through the nasal fossae (6). In these conditions, the aerosol does not first pass through the nostrils and its deposition efficiency is increased.

Based on this principle, different configurations of implementing the method can be created.

The mouthpiece according to the invention is airtight and penetrates beyond the teeth by a maximum length of 4 cm, constituting the means of administration of the aerosol for the nasal cavities, rhinopharynx or paranasal sinuses. This dimensional characteristic is specific to the invention as regards the conditions of application of the aerosol. The minimum penetration length of the mouthpiece beyond the patient's teeth is 1 cm.

A second configuration of the principle of the method of administration of the aerosol with a spray type device activated manually and not permitting either expiration or inspiration through the mouth is shown in FIGS. 7, 8, 9 and 10.

In this configuration (FIG. 7), the device (15) is a sealed circuit connected to the patient's mouth (8) comprising a mouthpiece (10) connected to a particle generator (12) operating without the addition of gas.

Thus, the system (15) is a sealed circuit allowing inspiration and expiration only through the nose. During the nasal inspiratory or expiratory phase (FIG. 7), the soft palate (16) closes the back of the oral cavity (14), isolating it from the lower (4) and upper (3) airways. The patient can then trigger (by manual pressure (13) on the device for example) the generation of the aerosol during the inspiration phase (FIG. 8) without aerosol being delivered into the patient's lungs (4). The patient can then perform an apnea (FIG. 9) then a closing movement of the oral cavity (14) from the front backwards (with the jaw for example) in order to create a change in volume so as to generate an overpressure and move the aerosol to the rhinopharynx (7). The patient can then expire (FIG. 10) through the nose to convey the particles from the rhinopharynx (7) to the nostrils (2), passing through the nasal fossae (6).

Figure 13:
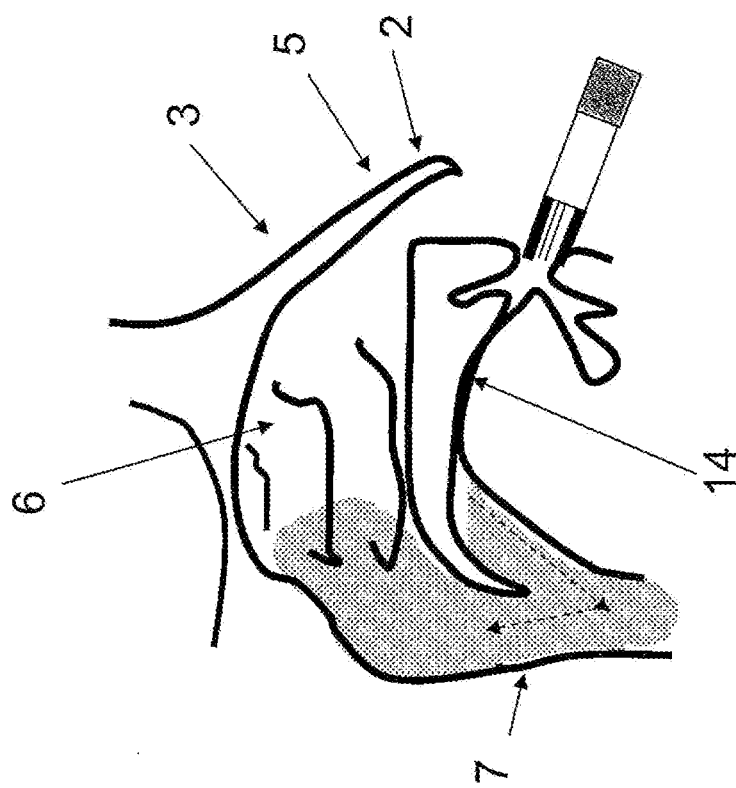

A third configuration of the principle of the method of administration of the aerosol with a valved spray type device activated manually and not allowing expiration through the mouth is shown in FIGS. 11, 12, 13 and 14. In this configuration (FIG. 11), the device (17) is a circuit connected to the patient's mouth (8) by means of a mouthpiece (10). This device (17) comprises a particle generator (12) operating without the addition of gas and an inspiratory valve (18). Thus, the system (17) is a circuit permitting inspiration through the nose and mouth but allowing only expiration through the nose. During the inspiratory phase (FIG. 11), the patient can inspire freely through the mouth (8) via the valve (18) or through the nose (2). The patient must not trigger the administration of the aerosol. The air inspired and penetrating into the patient's lungs (4) contains no aerosol. After the inspiratory phase, the patient performs an apnea (FIG. 12), and must simultaneously trigger the administration of the aerosol (by manual pressure (13) on the device (17) for example). The particles are generated at the patient's mouth (8) and are conveyed by their initial speeds to the oral cavity (14) and the rhinopharynx (7). He then performs a movement to close the oral cavity (14) from the front backwards (with the jaw for example) in order to create a change in volume so as to generate an overpressure and move the aerosol to the rhinopharynx (7) (FIG. 13). The patient can then expire (FIG. 14) freely through the nose to convey the particles from the rhinopharynx (7) to the nostrils (2), passing through the nasal fossae (6).

A fourth configuration of the system is shown in FIGS. 15 and 16 and concerns the principle of operation of the system according to the invention with a powder type generator and an external gas reservoir for the manual delivery of the aerosol. In this configuration (FIG. 15), the device (19) is a sealed circuit connected to the patient's mouth (8) comprising a mouthpiece (10) connected to a particle generator (20) (micronized powder for example) operating with the aid of an external gas reservoir (21) (deformable bulb for example).

Thus, the system (19) is a sealed circuit allowing only inspiration and expiration through the nose (2). During the inspiratory phase (FIG. 15), the patient can only inspire through the nose (2). The aerosol is not generated. The air inspired and penetrating into the patient's lungs (4) contains no aerosol. During the expiratory phase (FIG. 16), the patient can only expire through the nose (2). During his nasal expiration, the patient must trigger the generation of the aerosol by manual pressure (13) on the bulb (21) of the device (19). The particles are generated at the patient's mouth (8) and are conveyed by the gas contained in the reservoir (21) (bulb) to the rhinopharynx (7). The air expired by the patient is then added to the vector gas coming from the device (19) to convey the particles from the rhinopharynx (7) to the nostrils (2), passing through the nasal fossae (6).

Figure 17:
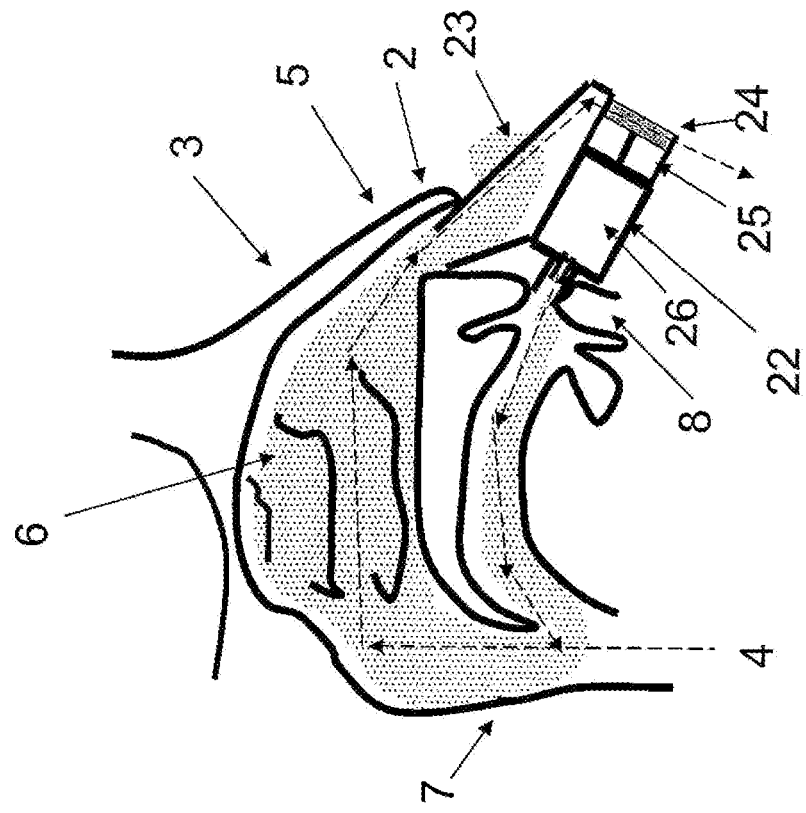
FIGS. 17 and 18 show the principle of operation of the system according to the invention with a pressurised bottle type generator and an external gas reservoir for the automatic delivery of the aerosol.
Figure 18:
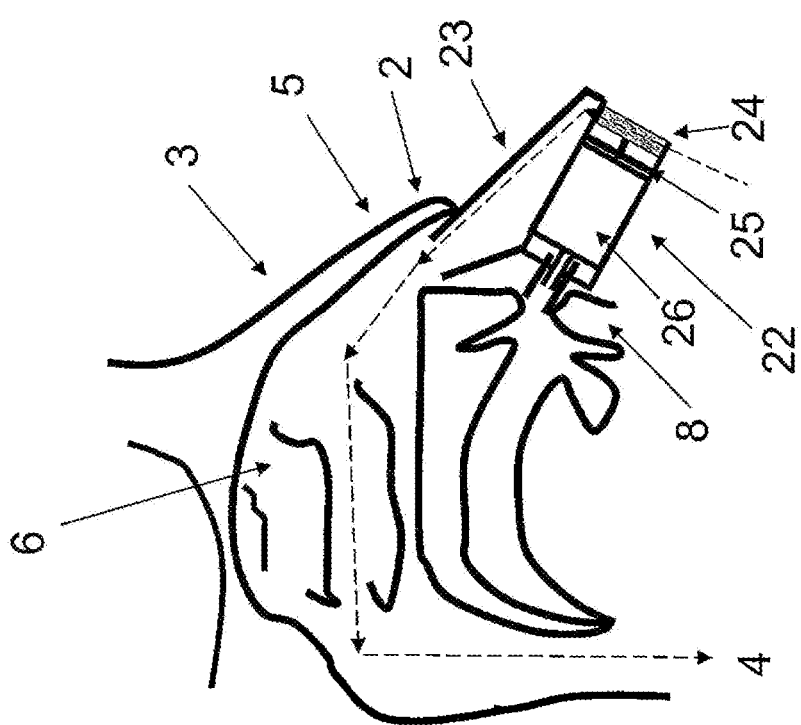

A fifth configuration of the system is shown in FIGS. 17 and 18 and concerns the principle of operation of the system according to the invention with a pressurised-bottle type generator and an external gas reservoir for the automatic delivery of the aerosol. In this configuration, the device (22) is connected to the patient's mouth (8) and has a nosepiece (23) connected to the patient's nostrils (2). The nosepiece (23) is connected to a mechanical means (24) permitting the triggering of a piston (25) during the patient's nasal expiration phase. The piston (25) permits the triggering of the administration of the aerosol by pressure on the aerosol generator (26) comprising a mixture of liquid and gas under pressure (pressurised bottle for example), the assembly forming a sealed assembly at the patient's mouth and permitting only nasal respiration. During the inspiratory phase (FIG. 17), the patient can only inspire through the nose (2). The mechanical means (24) does not trigger the piston (25): the aerosol is not generated. The air inspired and penetrating into the patient's lungs (4) contains no aerosol. During the expiratory phase (FIG. 18), the patient can only expire through the nose (2). The mechanical means (24) detect an overpressure, the piston (25) is triggered, the pressure on the aerosol generator (26) is exerted and the aerosol is expelled thanks to the pressurised gas contained in the aerosol generator (26) from the patient's mouth (8) to the rhinopharynx (7). The air expired by the patient and coming from his lungs (4) is added to the flow of gas coming from the aerosol generator (26). The aerosol is then directed from the rhinopharynx (7) to the nostrils (2) then expelled out of the patient.

Figure 20:
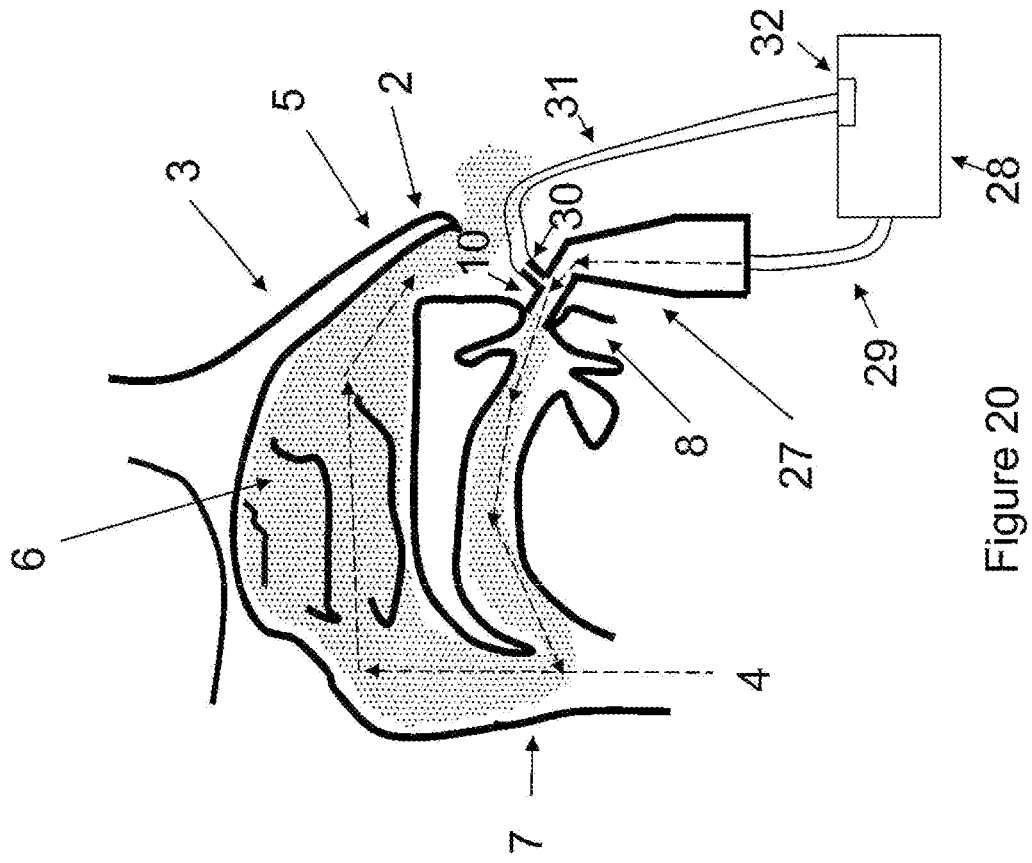
FIGS. 19 and 20 show the principle of operation of the system in its application with a pneumatic nebulizer and an automatic means of administration of the particles.
Figure 19:
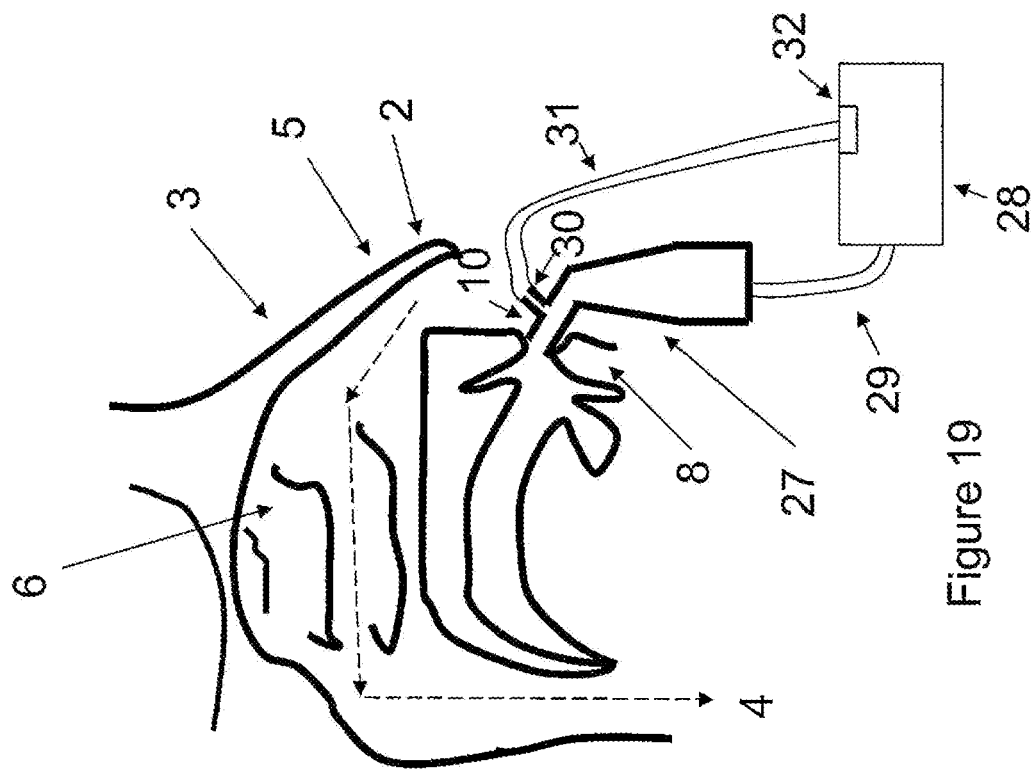

A sixth configuration of the system is shown in FIGS. 19 and 20 and concerns the principle of operation of the system in its application with a pneumatic nebulizer and an automatic particle administration means. In this configuration, the pneumatic nebulizer (27) is connected to the patient's mouth (8) and is supplied by an air compressor (28) via a tube (29). The nebulizer also has a connection (30) near the mouthpiece (10) designed to receive a tube (31) itself connected to the pressure sensor (32) contained in the compressor (28). The assembly forming a sealed assembly at the patient's mouth. Thus, during the patient's inspiratory phase (FIG. 19), the patient can only inspire through the nose, the pressure sensor (32) detects no overpressure, the aerosol is not generated. During the patient's expiratory phase (FIG. 20), the patient can only expire through the nose. The pressure sensor (32) detects an overpressure, the compressor (28) supplies pressure to the nebulizer (27) and the aerosol is generated. The aerosol produced is then conveyed by the air of the compressor (28) from the patient's mouth (8) to the rhinopharynx (7). The air expired by the patient and coming from his lungs (4) is added to the flow of air coming from the compressor (28). The aerosol is then directed from the rhinopharynx (7) to the nostrils (2) then expelled out of the patient.

Figure 22:
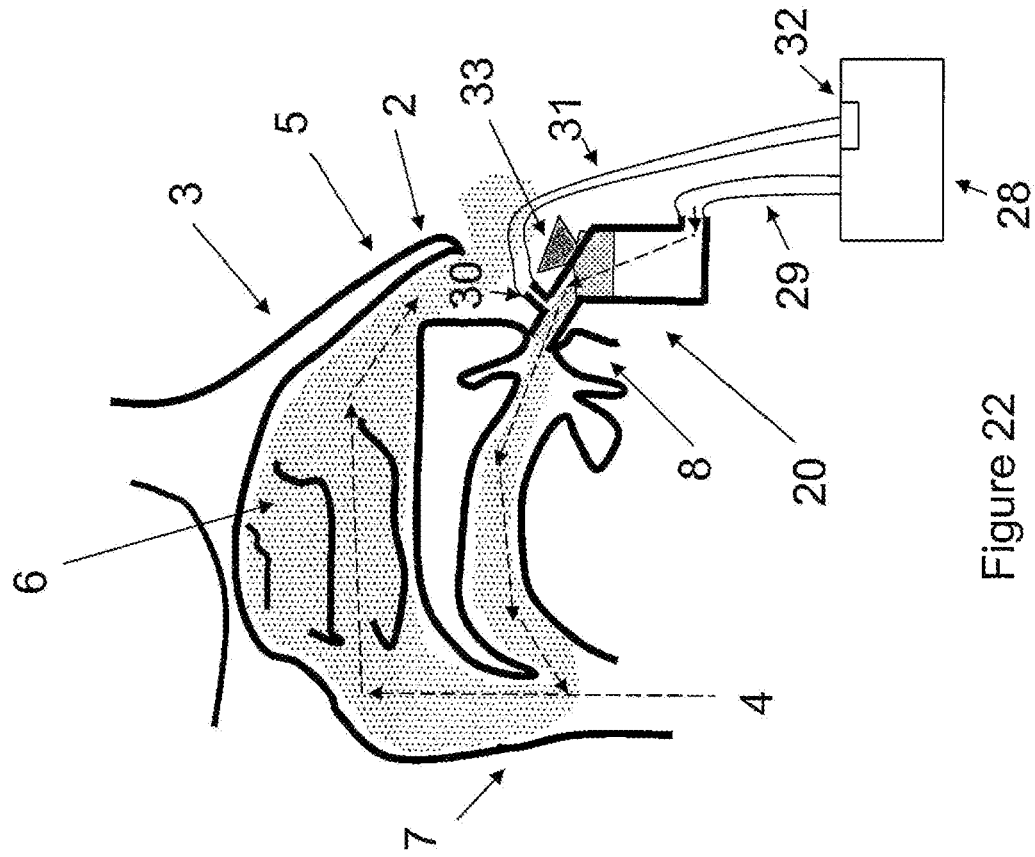
FIGS. 21 and 22 show the principle of operation of the system in its application with a nebulizer having a sieve, and a storage chamber associated with an automatic means of administration of the particles.
Figure 21:
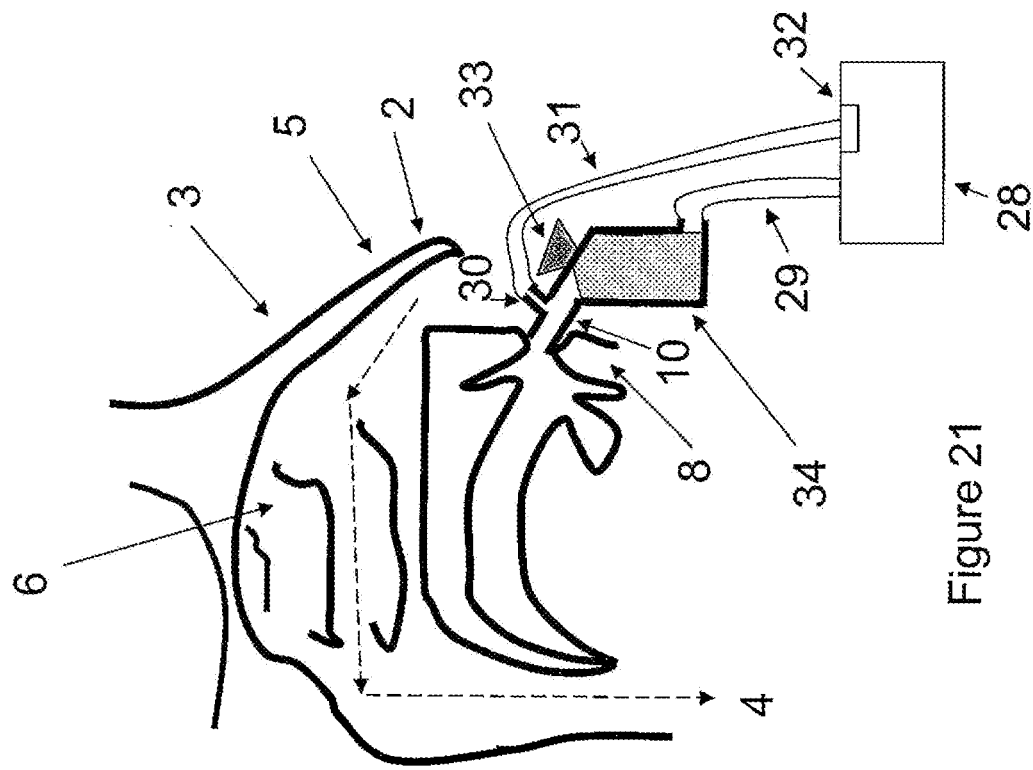
Figure 24:
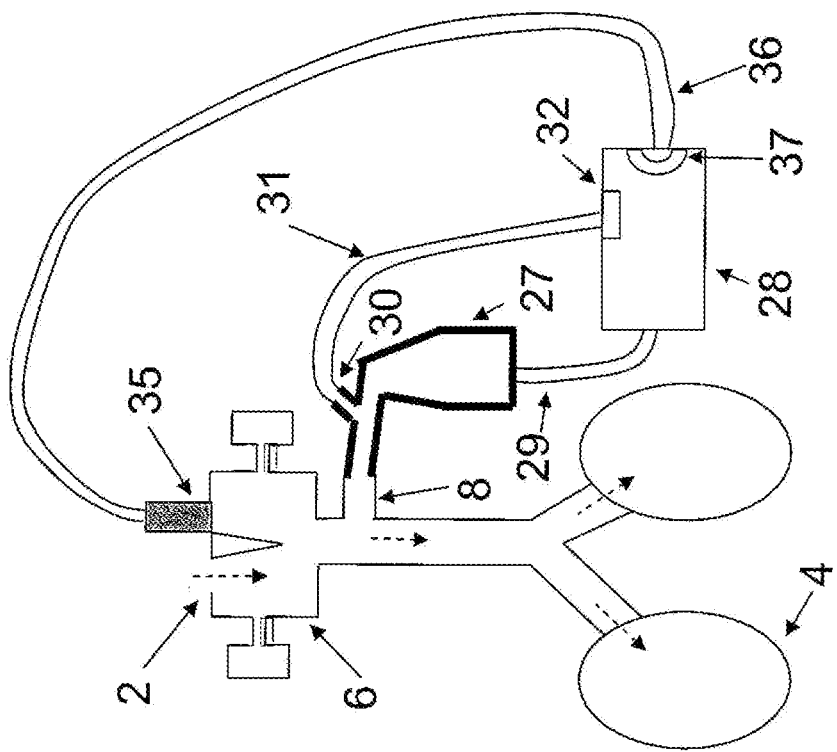
FIGS. 23, 24, 25 and 26 show the principle of operation of the system in its application with a pneumatic nebulizer associated with an acoustic wave and an automatic means of administration of the particles.
Figure 23:
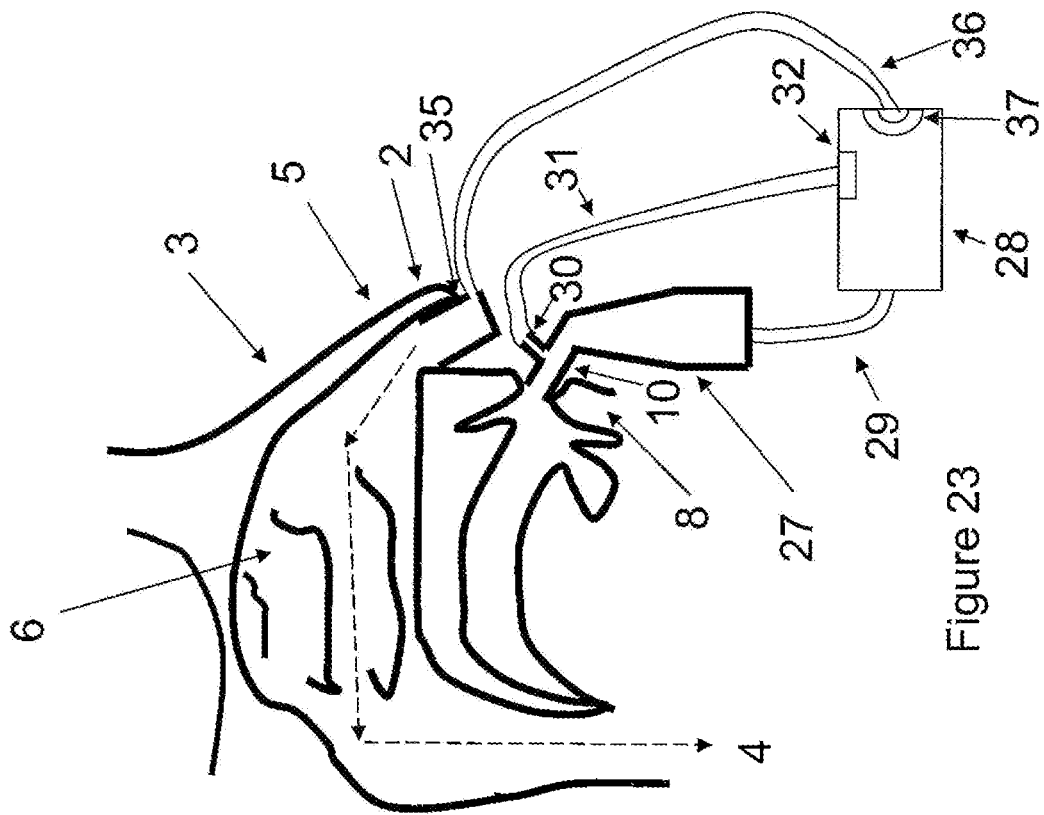
Figure 26:
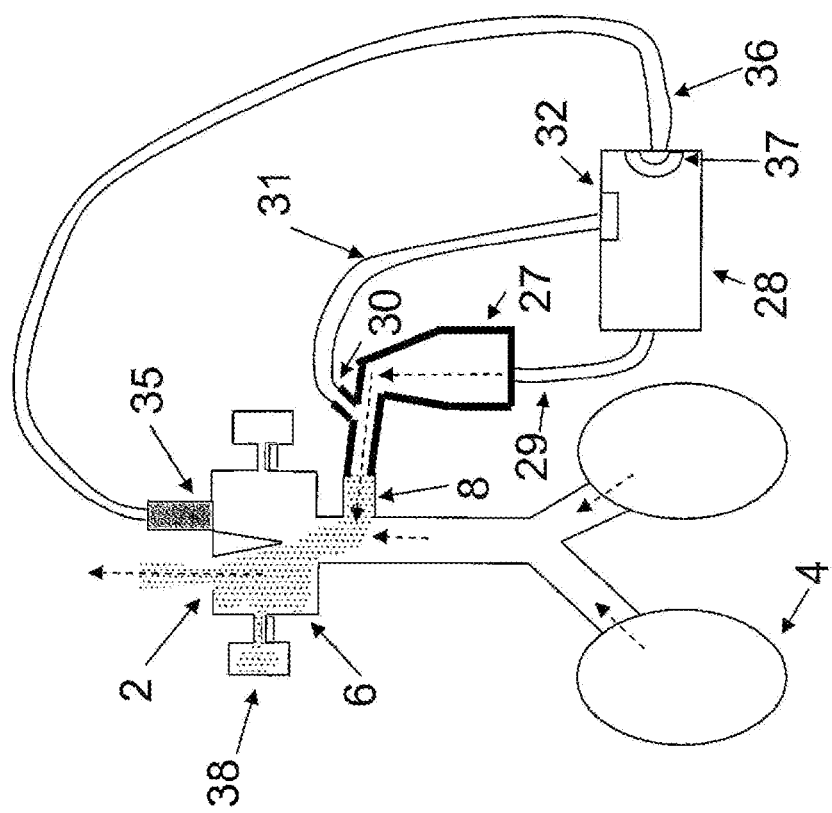
Figure 25:
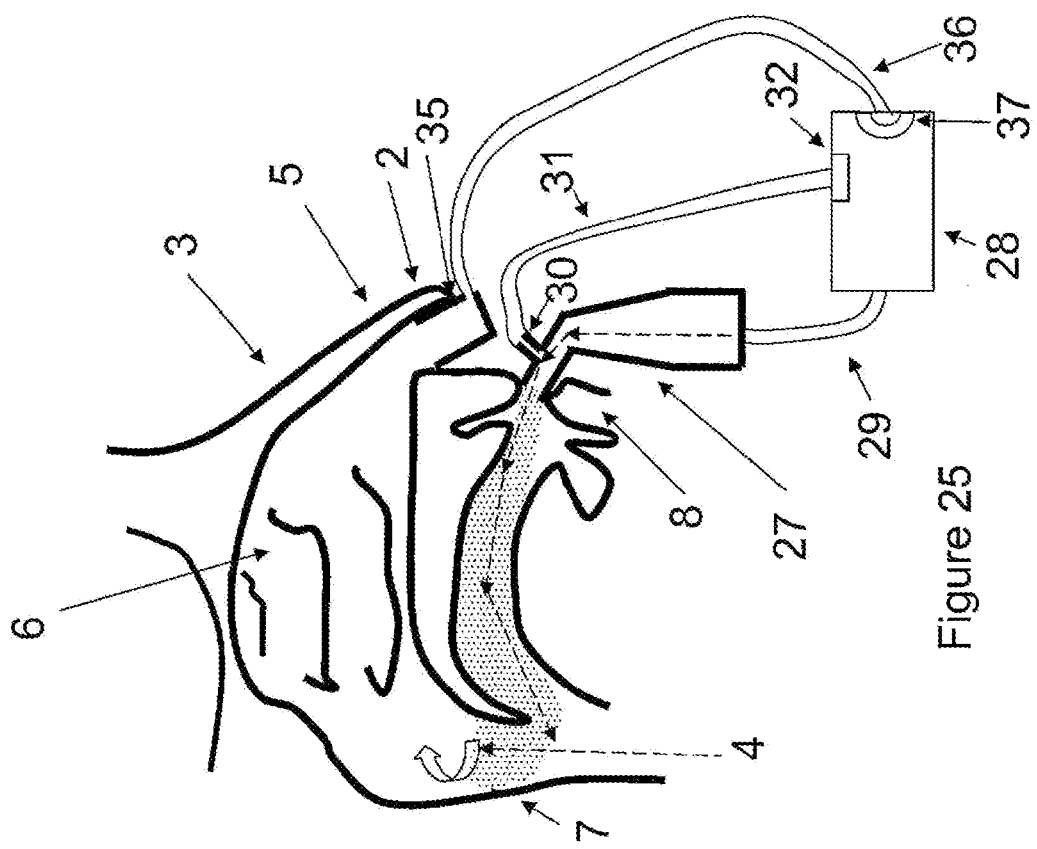
Figure 28:
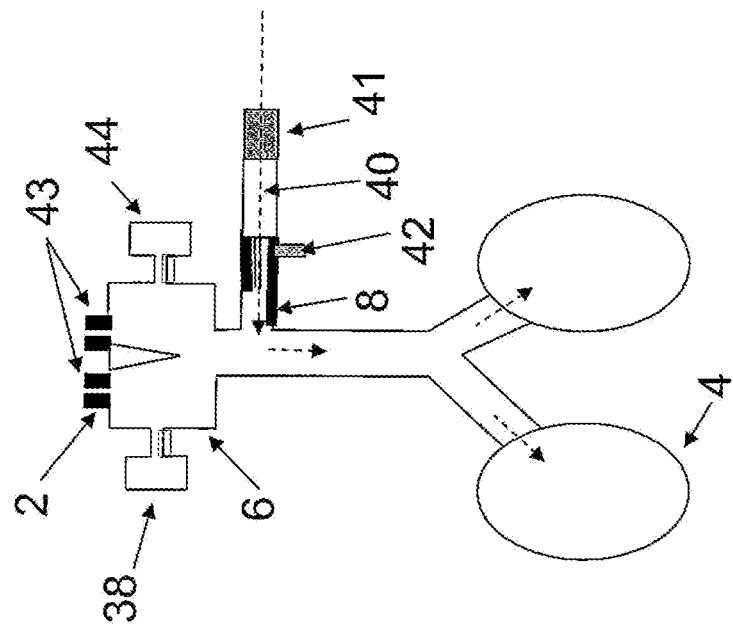
FIGS. 27, 28, 29 and 30 show the principle of operation of the system in its application with an external gas reservoir for the automatic delivery of the aerosol associated with a nosepiece creating an overpressure in the nasal fossae in order for the aerosol to penetrate into the maxillary sinuses.
Figure 27:
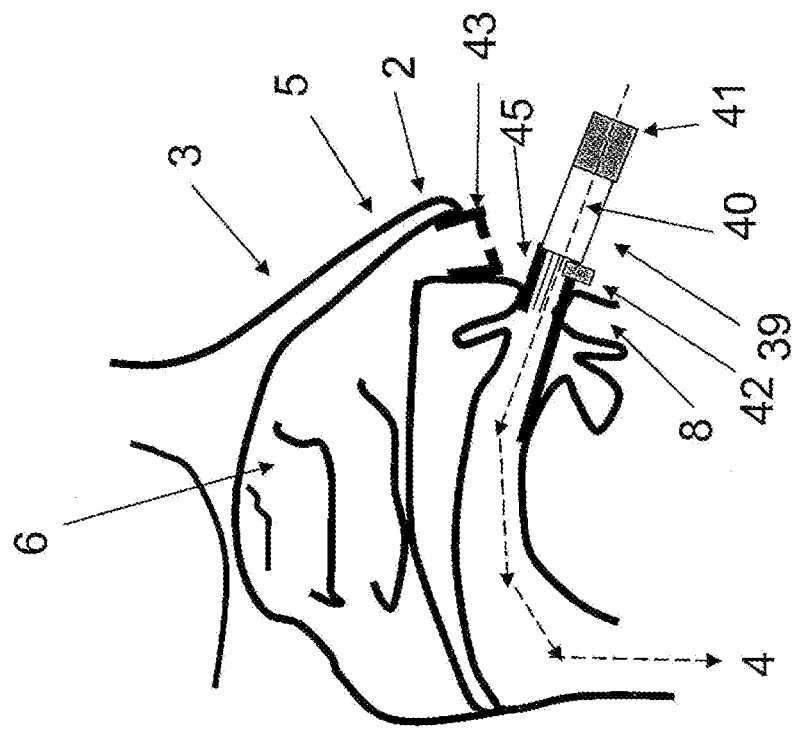
Figure 30:
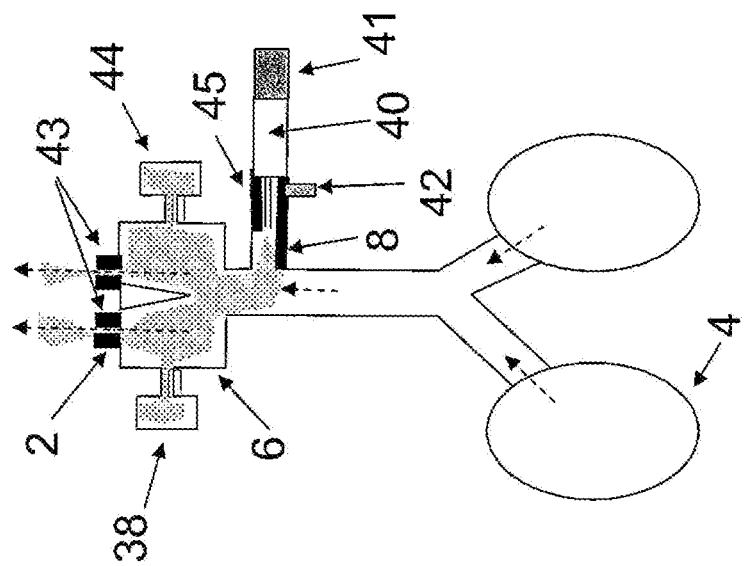
Figure 29:
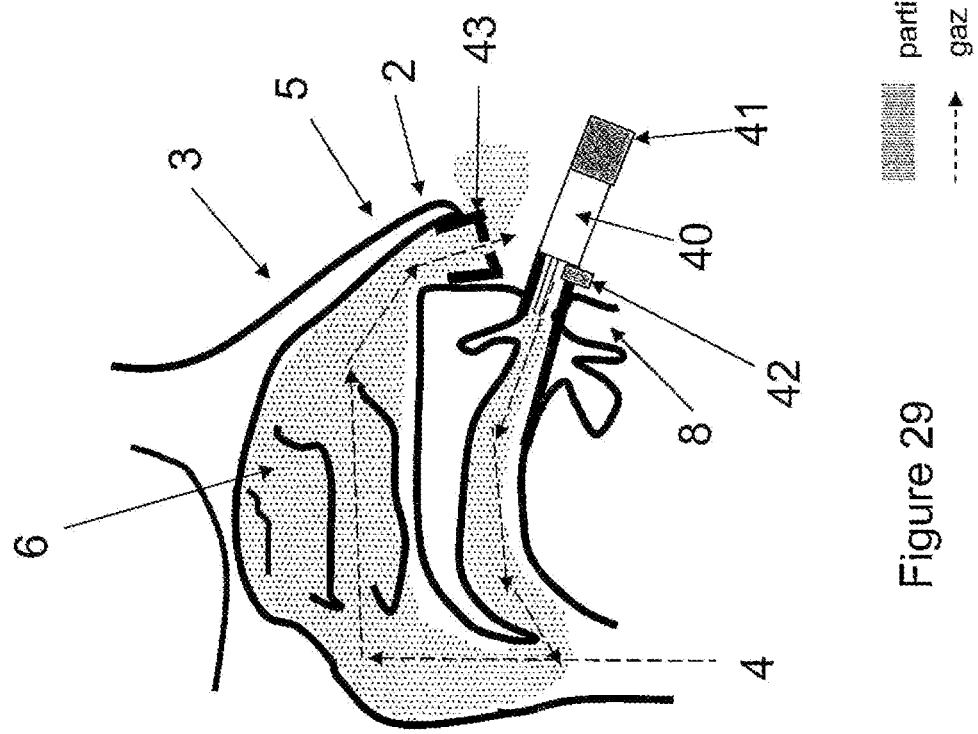

A seventh configuration of the system is shown in FIGS. 21 and 22 and concerns the principle of operation of the system in its application with a nebulizer and a storage chamber associated with an automatic particle-administration means.

In this configuration, a sieve, or ultrasonic, nebulizer (33) is associated with a storage chamber (34) connected at one end to the mouth (8) and at the other end to an air source (28) (compressor or ventilator for example). The nebulizer also has a connection (30) near the mouthpiece (10) designed to receive a tube (31) itself connected to the pressure sensor (32) contained in the air source (28), the assembly forming a sealed assembly at the patient's mouth. Thus, during the patient's inspiratory phase (FIG. 21), the patient can only inspire through the nose, the pressure sensor (32) detects no overpressure, the air from source (28) is not generated. The aerosol is produced continuously in the storage chamber (34). During the patient's expiratory phase (FIG. 22), the patient can expire only through the nose. The pressure sensor (32) detects an overpressure, the source (28) produces air in the storage chamber (34) and the stored aerosol is set in motion. The aerosol is then conveyed by air from the source (28) from the patient's mouth (8) to the back of the rhinopharynx (7). The air expired by the patient and coming from his lungs (4) is added to the airflow coming from the source (28). The aerosol is then directed from the rhinopharynx (7) to the nostrils (2) and is then expelled out of the patient.

An eighth configuration of the system is shown in FIGS. 23, 24, 25 and 26 and concerns the principle of operation of the system in its application with a pneumatic nebulizer associated with an acoustic wave and an automatic particle-administration means. In this configuration, the pneumatic nebulizer (27) connected to the mouth (8) is supplied by an air compressor (28) via a tube (29). The nebulizer also has a connection (30) near the mouthpiece (10) designed to receive a tube (31) itself connected to the pressure sensor (32) contained in the compressor (28), the assembly forming a sealed assembly at the patient's mouth. A nosepiece (35) is also connected to one of the two nostrils (2). A tube (36) designed to convey the acoustic waves connects the source of acoustic waves (37) and the nosepiece (35). Thus, during the patient's inspiratory phase (FIGS. 23 and 24), the patient can inspire through only one nostril, the pressure sensor (32) detects no overpressure, the aerosol is not generated. During the patient's expiratory phase (FIGS. 25 and 26), the patient can expire through only one nostril. The pressure sensor (32) detects an overpressure, the compressor (28) supplies pressure to the nebulizer (27) and the acoustic wave is produced from the acoustic wave source (37) to the nosepiece (35). The aerosol produced is then conveyed by the air of the compressor (28) from the patient's mouth (8) to the rhinopharynx (7). The air expired by the patient and coming from his lungs (4) is added to the flow of air coming from the compressor (28). The acoustic wave coming from the first nostril is transmitted to the rhinopharynx and the particle, gas and wave assembly is directed to the nasal fossae (6). The acoustic wave creating an acoustic pressure then promotes the penetration of the aerosol into the sinus (38). The aerosol is then directed to the open nostril then expelled out of the patient.

A ninth configuration of the system is shown in FIGS. 27, 28, 29 and 30 and concerns the principle of operation of the system in its application with an external gas reservoir associated with a nosepiece creating an overpressure in the nasal fossae in order for the aerosol to penetrate into the maxillary sinuses. The device (39) is a circuit connected to the patient's mouth (8) via a mouthpiece (45) penetrating beyond the patient's teeth by a minimum length of 1 cm (2 cm for example) in order to guarantee the opening of the oral cavity for the passage of the aerosol. This device (39) comprises an aerosol generator (40) including particles and pressurized gas, an inspiratory valve (41) as well as a pressure sensor (42) allowing triggering of the aerosol during the expiratory phase. A nosepiece (43) having a narrow section is also connected to both nostrils (2). Thus the system (39 and 43) is a circuit permitting and promoting inspiration through the mouth but also allowing only expiration through the nose. During the inspiratory phase (FIGS. 27 and 28), the patient inspires through the mouth (8) via the valve (41). The sensor (42) detects no overpressure: the aerosol is not generated. The air inspired and penetrating into the patient's lungs (4) contains no aerosol. During the expiratory phase (FIGS. 29 and 30), the valve (41) is closed and the patient can expire only through the nose (2). During his nasal expiration, the pressure sensor (42) detects an overpressure in the airways and the aerosol is generated by the aerosol generator (4). The particles are generated at the patient's mouth (8) and are conveyed by the propulsion gas of the aerosol generator (40) to the rhinopharynx (7). The air expired by the patient then conveys the particles from the rhinopharynx (7) to the nostrils (2), passing through the nasal fossae (6). The narrow section of the nosepiece (43) creates an overpressure at the upper airways and promotes the penetration of the aerosol into the sinuses (38 and 44). The aerosol is then directed to the nostrils then expelled out of the patient.

A tenth configuration of the system is shown in FIGS. 31, 32, 33 and 34 and concerns the principle of operation of the system according to the invention with a powder generator and an external gas reservoir for the manual delivery of aerosol during the first part of the inspiratory pause. In this configuration (FIG. 31), the device (46) is a sealed circuit connected to the patient's mouth (8) comprising a mouthpiece (10) connected to a generator (47) of particles (micronized powder for example) operating with the aid of an external gas reservoir (21) (deformable bulb for example) administering the particles of powder only during the first period of generation of gas by deformation of the bulb.

Figure 34:
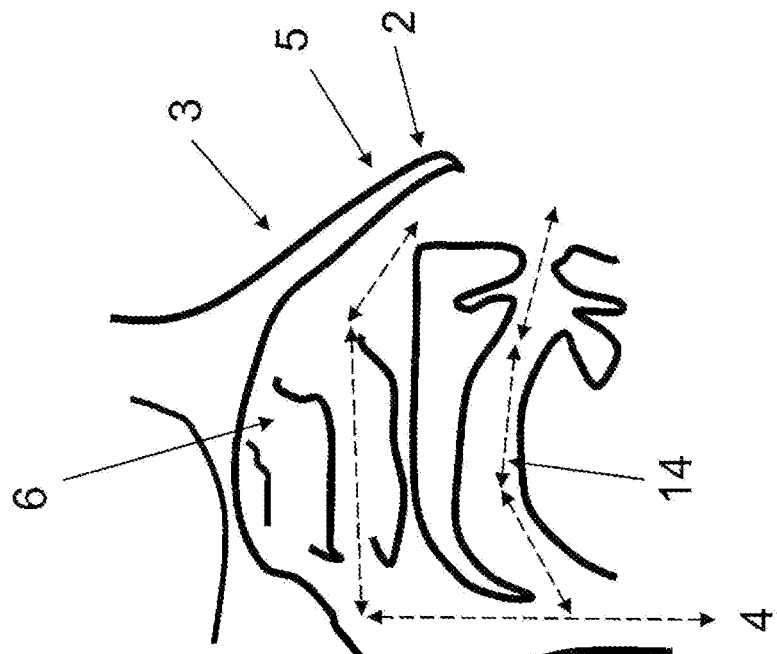
Figure 33:
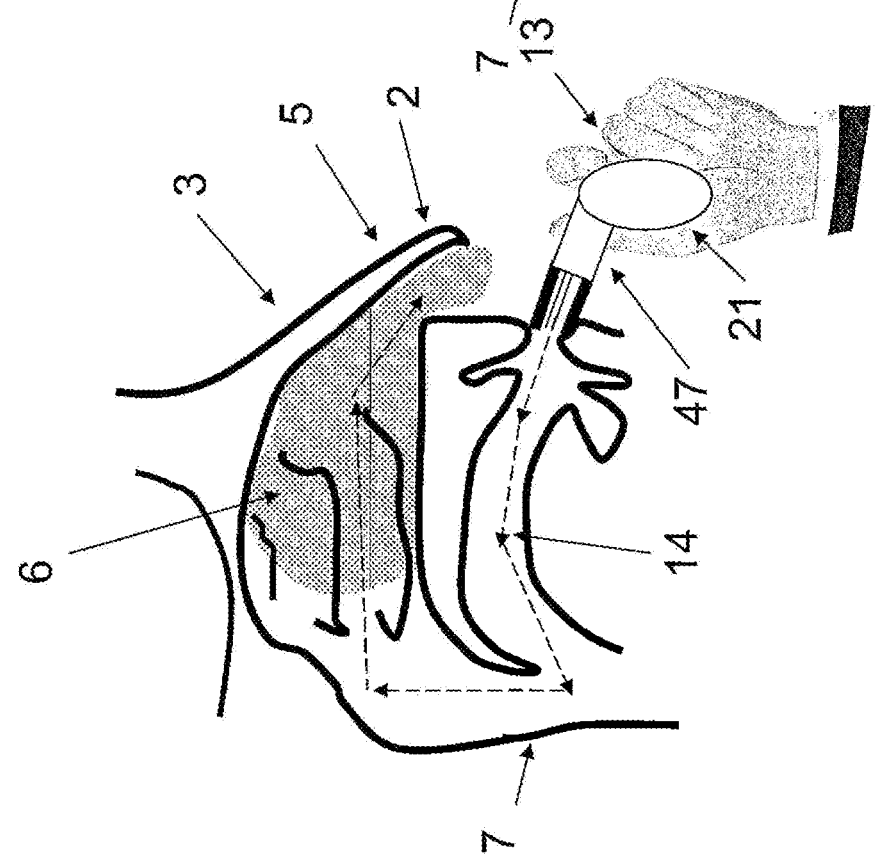

Thus, the system (46) is a sealed circuit allowing only inspiration and expiration through the nose (2). During the inspiratory phase (FIG. 31), the patient can only inspire through the nose (2). The aerosol is not generated. The air inspired and penetrating into the patient's lungs (4) contains no aerosol. The patient then performs a respiratory pause (FIG. 32) and simultaneously triggers the generation of the aerosol by manual pressure (13) on the bulb (21) of the device (46). During the first part of the inspiratory pause, the particles are generated at the patient's mouth (8) and are conveyed by the gas contained in the reservoir (21) (bulb) to the nostrils (7). During the second part of the respiratory pause (FIG. 33), the gas produced by the bulb (21) and generated at the patient's mouth (8) contains no particles. The gas containing no particles fills the mouth, the rhinopharynx, the nasal fossae then the nostrils, thus ensuring the flushing of this area by the gas containing no particles in suspension. The patient can then expire or inspire freely through the nose or the mouth a gas containing no particles (FIG. 34). In this configuration, the aerosol is not generated in the patient's lungs (4) and the speed of the particles produced can be controlled by the flow of the gas generator (21).

In the above-mentioned configurations, the forms of the circuits can vary in form, the Figures having been described and given by way of example. The use of a device not comprising a system of delivering gas to convey the particles of medication requires an active participation of the patient. After the delivery of the medication into the oral cavity, the patient must bring about a change in his mouth's internal volume (by swallowing or by closing the jaw) in order to move the particles from the oral cavity to the rhinopharynx then must expire through the nose. This principle of the method of administration of aerosol for the rhinopharynx, paranasal sinuses or nasal cavities is described in the first, second and third configuration. The use of a device comprising a system of gas delivery for the particles in order to convey the medication requires a less active participation of the patient. In this case, the patient must only synchronise the manual delivery of the aerosol with his nasal expiration or his respiratory pause. This principle of operation of the aerosol system for the rhinopharynx, paranasal sinuses or nasal cavities is described in the fourth and tenth configurations. This system also has the advantage of being very simple to use and could be compared to the principle of metered-dose aerosols (pMDI) requiring both mouth inspiration and a manual triggering reflex to administer the aerosol during its inspiration phase. In order to limit any incorrect use of the device in its simplest form, the use of a inspiratory valve (configuration 9) or a sealed device at the patient's mouth (configurations 4, 5, 6, 7, 8 and 10) are used so as not to permit expiration from the mouth during the aerosol-administration phases. Similarly, the use of an automatic means for the administration of the aerosol during the non-inspiratory phase (expiratory phase or respiratory pause phase) can be used in order to overcome the problem of the patient's manual reflex (configurations 5, 6, 7, 8 and 9). Consequently, the means enabling the administration of particles into the mouth can be an automatic means or a non-automatic means (for example: manual means activated by the patient himself or another person). The type of aerosol generator may vary. An aerosol generator of the pneumatic, ultrasonic or sieve type nebulizer can be used. Similarly, any other liquid or solid aerosol generator can be used (dry powder inhaler or metered-dose inhaler). A piston system followed by an injector (spray, microsprayer, etc.) or even a system of pre-loading powder into a tube or into a capsule can also be used. An additional nosepiece can also be used to transmit a wave or create an overpressure. The administration of the aerosol can be performed during all or part of the nasal expiration phases or respiratory pause phases.

Figure 35:
FIG. 35 represents the scintigraphic imagery of the deposition of the aerosol according to the invention.
Figure 36:
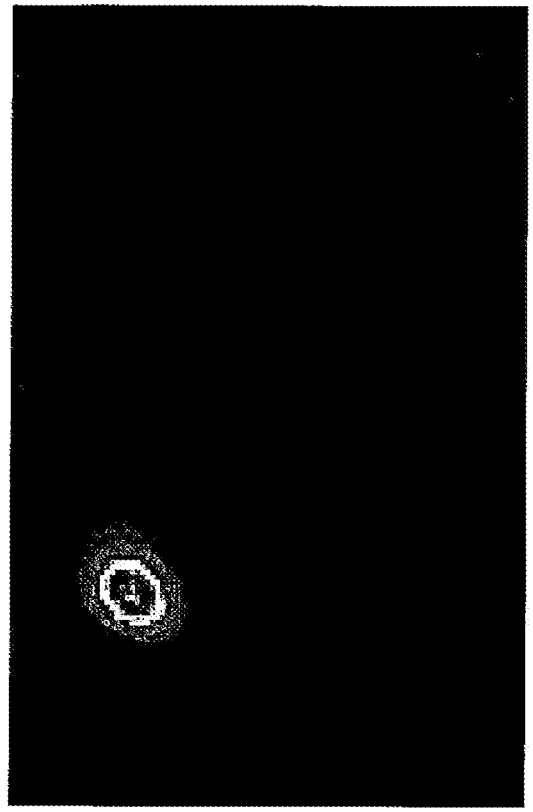
FIG. 36 represent the scintigraphic imagery of the deposition of the aerosol with a nebulizer delivering the aerosol by means of a nosepiece.

According to any of the above-described configurations, the solution appears to be extremely advantageous because, according to the tests conducted, measurements confirm that the dose of radioactive aerosol deposited in the nasal fossae is significantly increased compared to the dose of radioactive aerosol deposited in the nostrils (Table 2) (FIGS. 35 and 36).

TABLE 2

Ratio of aerosol deposited in the nasal fossae to aerosol deposited in the nostrils. Study of the distribution of radioactive aerosol in the ENT environment of healthy patients.

| | Atomisor NL11 Nebulizer Nasal Administration | Invention Oral Administration |
| --- | --- | --- |
| 1 | 0.01 | 1.43 |
| 2 | 0.1 | 1.35 |

The invention claimed is:

1. Aerosol administration device comprising a generator of particles of size between 10 nm and 200 µm for forming an aerosol, a mouthpiece or oral mask for oral administration of the aerosol initially into a mouth of a patient during a nasal expiration phase or during a respiratory pause phase preceding nasal expiration, and a source of gas or pressure for conveying the particles, wherein the particle generator is operated manually or automatically, the mouthpiece and particle generator constitute an airtight assembly adapted to be connected to the mouth of the patient during aerosol administration phases, the mouthpiece penetrates beyond teeth of the patient by a maximum length of 4 cm and administers aerosol, starting in the mouth, for the nasal cavities, rhinopharynx or paranasal sinuses during the aerosol administration phases, such that the aerosol is successively conveyed from the mouthpiece to the mouth, then the rhinopharynx, then the nasal fossae and sinuses, and then said aerosol escapes through one or both nostrils of the patient, and the device does not allow expiration through the mouth of the patient during the aerosol administration phases.

2. Device according to claim 1, wherein the mouthpiece is airtight and penetrates beyond the teeth by a minimum length of 1 cm.

3. Device according to claim 1, wherein triggering of the oral administration of the aerosol is achieved automatically with aid of an electric, pneumatic or mechanical means.

4. Device according to claim 3, wherein the means is adapted to be connected to the mouth and comprises a nosepiece adapted to be connected to the nostrils, and said nosepiece is connected to a mechanical means triggering a piston during the nasal expiration phase.

5. Device according to claim 3, wherein the generator comprises a pneumatic nebulizer adapted to be connected to the mouth supplied by an air compressor via a tube, said nebulizer being connected to the mouthpiece and to a tube connected to a pressure sensor contained in the air compressor, and the nebuliser is triggered during the nasal expiration phase, detected by the pressure sensor being adapted to be connected in a sealed manner to an oral cavity of the patient.

6. Device according to claim 3, wherein the generator includes a nebulizer and a storage chamber adapted to be connected to the mouth and to a source of gas, said nebulizer being connected to the mouthpiece and to a tube connected to a pressure sensor contained in the gas source, and the nebulizer is triggered during the nasal expiration phase, detected by the pressure sensor adapted to be connected in a sealed manner to an oral cavity of the patient.

7. Device according to claim 1, wherein the generator comprises a pneumatic nebulizer associated with an acoustic wave and particle-administration means, and said nebulizer is adapted to be connected to the mouth and supplied by an air compressor via a tube, said nebulizer having a connection near the mouthpiece to receive a tube connected to a pressure sensor contained in said air compressor, the assembly being adapted to be sealed at the mouth, and further comprising a nosepiece adapted to be connected to one of the nostrils, and a tube conveying acoustic waves connecting an acoustic-wave source and the nosepiece.

8. Device according to claim 1, wherein the mouthpiece is connected to a generator of particles of powder operating with aid of an external gas reservoir.

9. Device according to claim 1, wherein the generator of particles comprises a pneumatic nebuliser adapted to be connected to the mouth and supplied by an air compressor via a tube, said nebulizer having a connection near the mouthpiece to receive a tube connected to a pressure sensor contained in said air compressor, and the assembly is adapted to be sealed at the mouth.

10. Device according to claim 1, wherein the generator of particles comprises a nebulizer associated with a storage chamber adapted to be connected at a first end to the mouth and at a second end to an air source, and said nebulizer has a connection near the mouthpiece to receive a tube connected to a pressure sensor contained in the air source, the assembly being adapted to be sealed at the mouth.

11. Device according to claim 1, wherein the generator of particles and the source of gas or pressure comprises an aerosol generator including particles and pressurized gas, and further including an inspiratory valve and a pressure sensor triggering oral administration of the aerosol during the expiratory phase, and a nosepiece having a narrow section and connected to both nostrils of the patient.

12. Device according to claim 1, wherein the assembly defines a sealed circuit adapted to be connected to the mouth comprising the mouthpiece connected to a generator of particles of powder operating with aid of an external gas reservoir administering particles of powder only during a first period of generation of gas by deformation of said gas reservoir.

* * * * *